(12) United States Patent
Ma

(10) Patent No.: US 9,880,084 B2
(45) Date of Patent: Jan. 30, 2018

(54) APPARATUS FOR SEPARATION OF PARTICLES

(75) Inventor: Hongshen Ma, Delta (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 368 days.

(21) Appl. No.: 14/112,021

(22) PCT Filed: Apr. 13, 2012

(86) PCT No.: PCT/CA2012/000362
§ 371 (c)(1),
(2), (4) Date: Jan. 6, 2014

(87) PCT Pub. No.: WO2012/139209
PCT Pub. Date: Oct. 18, 2012

(65) Prior Publication Data
US 2015/0300939 A1 Oct. 22, 2015

Related U.S. Application Data

(60) Provisional application No. 61/476,151, filed on Apr. 15, 2011.

(51) Int. Cl.
*G01N 15/10* (2006.01)
*G01N 1/40* (2006.01)
*C12M 1/00* (2006.01)
*G01N 15/00* (2006.01)

(52) U.S. Cl.
CPC .......... *G01N 15/10* (2013.01); *G01N 1/4077* (2013.01); *C12M 47/04* (2013.01); *G01N 2015/008* (2013.01); *G01N 2015/0073* (2013.01); *G01N 2015/105* (2013.01)

(58) Field of Classification Search
CPC ................ G01N 15/10; G01N 1/4077; G01N 2015/0073; G01N 2015/008; G01N 2015/105
See application file for complete search history.

(56) References Cited

U.S. PATENT DOCUMENTS

| 2006/0051265 A1 | 3/2006 | Mohamed et al. |
| 2007/0161051 A1 | 7/2007 | Tsinberg et al. |
| 2009/0136982 A1 | 5/2009 | Tang et al. |
| 2011/0065181 A1 | 3/2011 | Hvichia et al. |

FOREIGN PATENT DOCUMENTS

WO 2007021409 A1 2/2007

OTHER PUBLICATIONS

International Search Report and Written Opinion dated Aug. 6, 2012 received in corresponding International application No. PCT/CA2012/000362.
McFaul et al., "Cell separation based on size and deformability using microfluidic funnel ratchets", Lab on a Chip, Apr. 19, 2012.
Loutherback, et al. "Deterministic Microfluidic Ratchet", Physical Review Letters, The American Physical Society, Jan. 30, 2009, PRL 102, 045301 (2009), pp. 045301-1-045301-4.
(Continued)

*Primary Examiner* — Samuel P Siefke
(74) *Attorney, Agent, or Firm* — Broden Ladner Gervais LLP; Todd Keeler

(57) ABSTRACT

Methods and apparatus for separation of particles based on deformability, and for measurement of particle deformability are provided.

16 Claims, 15 Drawing Sheets

(56) References Cited

OTHER PUBLICATIONS

Mohamed et al. "Isolation of tumor cells using size and deformation", Journal of Chromatography A, 1216 (2009), pp. 8289-8295.
Herricks, et al. "Deformability limits of Plasmodium falciparum-infected red blood cells", Cellular Microbiology, vol. 11(9), 2009, pp. 1340-1353.
Bow, et al. "A microfabricated deformability-based flow cytometer with application to malaria", Lab on a Chip, 2011, pp. 1065-1073.
Guo et al, "Microfluidic Micropipette Aspiration for Measuring the Deformability of Single Ceiis", Draft Paper, Lab on a Chip, The Royal Society of Chemistry Publishing.
Astumian, R.D., "Thermodynamics and kinetics of a Brownian motor", Science, vol. 276, May 9, 1997, pp. 917-922.
Gorre, L., E. et al. "Rectified motion of a mercury drop in an asymmetric structure", Europhysics Letters, vol. 33(4), Feb. 1, 1996, pp. 267-272.
Unger, M.A., et al., "Monolithic microfabricated valves and pumps by multilayer soft lithography", Science, vol. 288. Apr. 7, 2000, pp. 113-116.
Cranston, H.A., et al., "Plasmodium-Falciparum Maturation Abolishes Physiologic Red-Cell Deformability" American Associate for the Advancement of Science, vol. 223 (4634), Jan. 27, 1984, pp. 400-403.
Studer, V., et al., "Scaling properties of a low-actuation pressure microfiuidic valve", Journal of Applied Physics, vol. 95(1), Jan. 1, 2004, pp. 393-398.
Guo, Q., et al., "Microfluidic Biomechanical Assay for Red Blood Cells Parasitized by Plasmodium falciparum", Lab on a Chip, 2012, pp. 1143-1150.
Gauglitz et al., "Dynamics of Haines Jumps for Compressible Bubbles in Constricted Capillaries", American Institute of Chemical Engineers Journal, vol. 35 (2), Feb. 1989, pp. 230-240.
Hebbel, R.P., et al., "Oxidation-Induced Changes in Microrheologic Properties of the Red-Blood-Cell Membrane", Blood, vol. 76, 1990, pp. 1015-1020.
Guo, Q., et al., "Deterministic microfiuidic ratchet based on the deformation of individual cells", Physical Review E, vol. 83, 2011, pp. 051910-1-051910-5.
Needham, D. et al., "A Sensitive Measure of Surface Stress in the Resting Neutrophil", Biophysical Journal, vol. 61, Jun. 1992, pp. 1664-1670.
Meng, S., et al., "Circulating tumor cells in patients with breast cancer dormancy" Clinical Cancer Research, vol. 10, Dec. 15, 2004, p. 8152-8162.
Groisman, A., et al., "A microfluidic rectifier: Anisotropic flow resistance at low Reynolds numbers", Physical Review Letters, vol. 92(9), Mar. 5 2004, pp. 094501-1-094501-4.
Fehm, T., et al., "Methods for isolating circulating epithelial cells and criteria for their classification as carcinoma cells", Cytotherapy, vol. 7(2), 2005, pp. 171-185.
Kuo, J.S,, et 31,, "Deformability considerations in filtration of biological cells", Lab on a Chip, The Royal Society of Chemistry: 2010, vol. 10, pp. 837-842.
Yap, B. et al., "Cytoskeletal remodeling arid cellular activation during deformation of neutrophils into narrow channels", Journal of Applied Physiology, vol. 99, Aug. 5, 2005, DOI: 10.1152/japplphysiol.00503.2005, pp. 2323-2330.
Tinevez, J.Y., et at, "Role of cortical tension in bleb growth", Proceedings of the National Academy of Sciences of the Unites States of America, vol. 106 (44), Nov. 3, 2009, pp. 18581-18586.
Lim, C.T., et al., "Mechanical models for living cells—A review", Journal of Biomechanics, vol. 39, 2006, page 195-216.
Matthias, S. et al., "Asymmetric pores in a silicon membrane acting as massively parallel brownian ratchets", Nature, vol. 424, Jul. 3, 2003, pp. 53-57.
Hochmuth, R.M., "Micropipette aspiration of living cells", Journal of Biomechanics, vol. 33, 2000, pp. 15-22.
Faucheux, L.P., et al., "Optical Thermal Ratchet", Physical Review Letters, vol. 74(9), Feb. 27, 1990, pp. 1504-1507.
Davis, J.A., et al., "Deterministic hydrodynamics: Taking blood apart" Proceedings of the National Academy of Sciences of the United States of America, vol. 103(40), pp. 14779-14784.
Mahmud, G., et al., "Directing cell motions on micropatterned ratchets", Nature Physics, vol. 5, Aug. 2009, pp. 606-612.
Hulme, S.E., et al:, "Using ratchets and sorters to fractionate motile cells of *Escherichia coli* by length", Lab on a Chip, pp. 1888-1895.
Galajda, P. et al., "Funnel ratchets in biology at low Reynolds number choanotaxis", Journal of Modern Optics, vol. 55, Nos. 19-20, Nov. 10-20, 2008, pp. 3413-3422.
Rousselet, J., et al., "Directional Motion of Brownian Particles Induced by a Periodic Asymmetric Potential", Nature, vol. 370. Aug. 11, 1994, pp. 446-448.
Cross, S.E., et al., "AFM-based analysis of human metastatic cancer cells", Nanotechnology, vol. 19, 2008, pp. 1-8.
Gorre-Talini, L., et al., "Dielectrophoretic ratchets" Chaos, vol. 8(3), Sep. 1998, pp. 650-656.
Julicher, F., et al., "Modeling molecular motors", Reviews of Modern Physics, vol. 69(4), Oct. 1997, pp. 1269-1281.
Bader, J.S., et al., "DNA transport by a micromachined Brownian ratchet device", Proceedings of the National Academy of Sciences of the United States of America, vol. 96(23), Nov. 9, 1999, pp. 13165-13169.
Lam, W.A., et al., "Chemotherapy exposure increases leukemia cell stiffness", Blood, vol. 109(8), Apr. 15, 2007, pp. 3505-3508.
Suresh, S., et al., "Connections between single-cell biomechanics and human disease states: gastrointestinal cancer and malaria", Acta Biomaterialia, vol. 1, 2005, pp. 15-30.
Nash, G.E., et al., "Abnormalities in the Mechanical-Properties of Red Blood-Cells Caused by Plasmodium-Falciparum", Blood, vol. 74(2), Aug. 1, 1989, p. 855-861.
Haines, William B., "Studies in the physical properties of soil. V. The hysteresis effect in capillary properties, and the modes of moisture distribution associated therewith", Journal of Agricultural Science, Sep. 16, 1929, pp. 97-116.
Hebbel, R.P., "The Sickle Erythrocyte in Double Jeopardy: Autoxidation and Iron Decompartmentalization", Seminars in Hematology, vol. 27, No. 1, Jan. 1990, pp. 51-69.
Supplementary Partial European Search Report dated Nov. 18, 2014, issued against corresponding European Patent Application No. 12771679.3.
Sven Matthias et al.: "Asymmetric pores in a silicon membrane acting as massively parallel brownian ratchets", Nature, vol. 424, No. 6944, Jul. 3, 2003, pp. 53-57.
T. Fehm et al.: "Methods for isolating circulating epithelial cells and criteria for their classification as carcinoma cells", Cytotherapy, vol. 7, No. 2, May 1, 2005, pp. 171-185.
Jason S. Kuo et al.: "Deformability considerations in filtration of biological cells", Lab on a Chip, vol. 10, No. 7, Jan. 1, 2010, p. 837.
S. Elizabeth Hulme et al.: "Using ratchets and sorters to fractionate motile cells of *Escherichia coli* by length", Lab on a Chip, vol. 8, No. 11, Jan. 1, 2008, p. 1888.

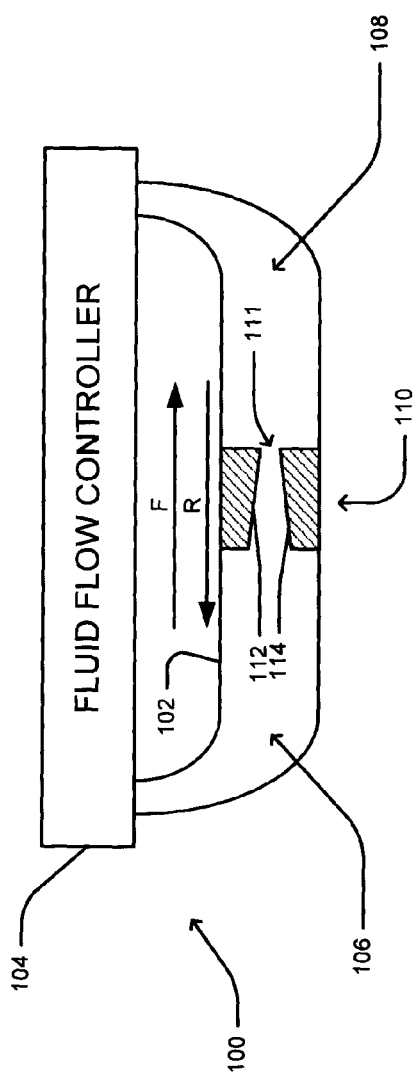
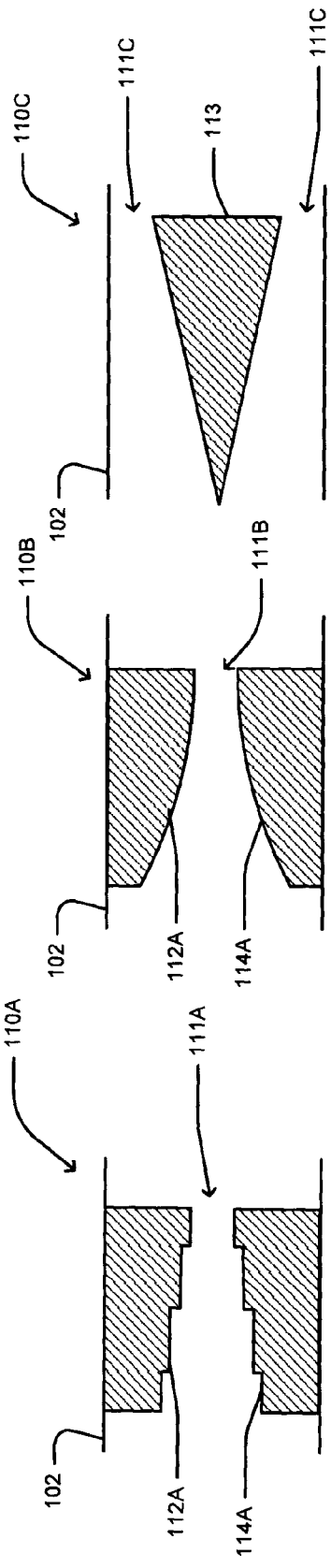
Figure 1
Figure 1A
Figure 1B
Figure 1C

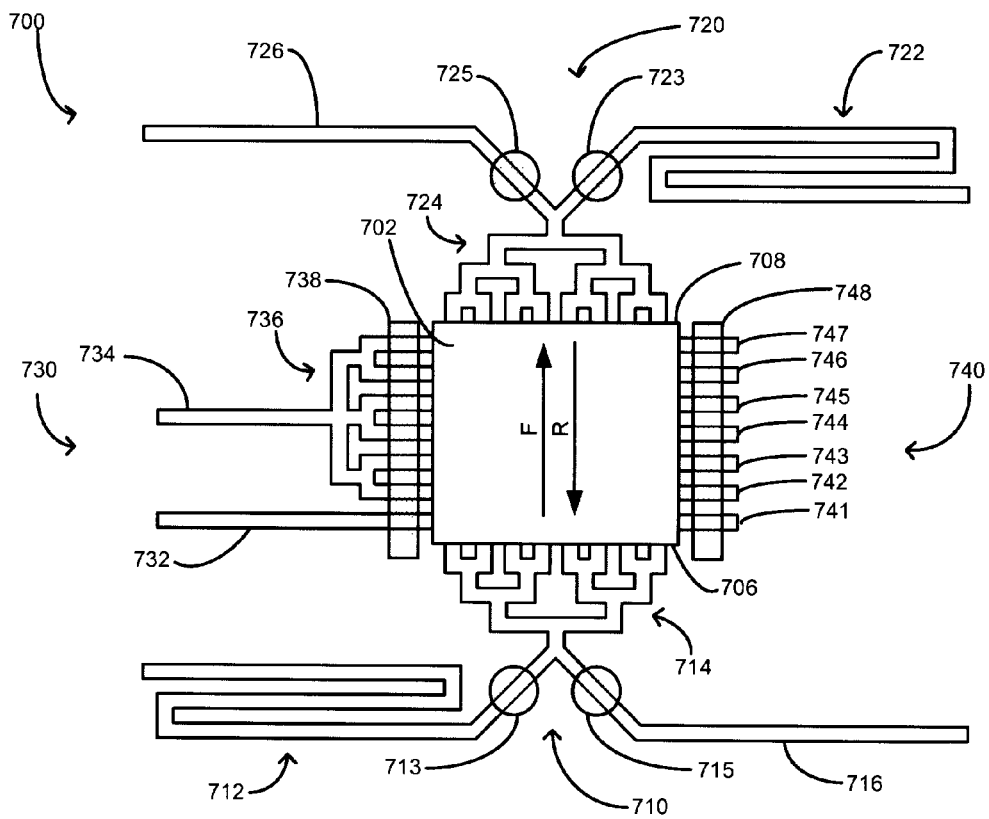
Figure 7A
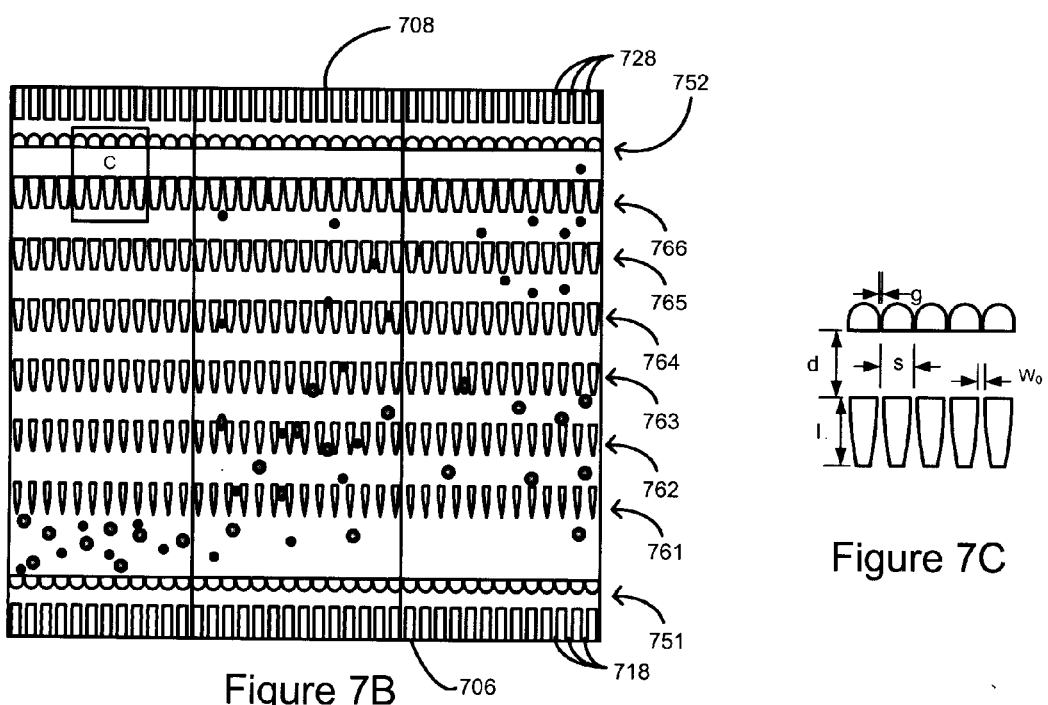
Figure 7B
Figure 7C

Figure 8B          Figure 8C
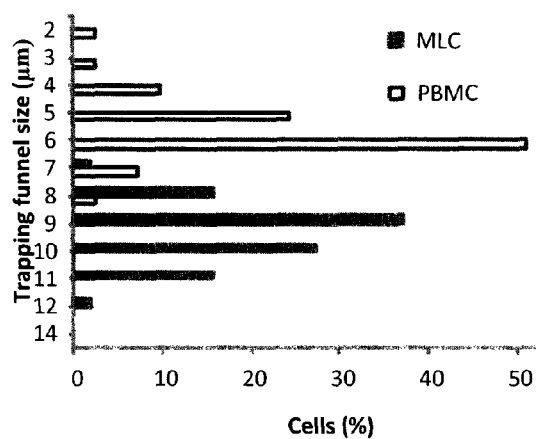          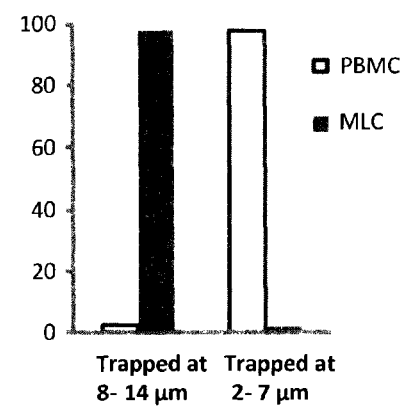
Figure 8A          Figure 8D

APPARATUS FOR SEPARATION OF PARTICLES

CROSS REFERENCE TO RELATED APPLICATIONS

This application claims the benefit of priority of U.S. Provisional Patent Application No. 61/476,151 filed Apr. 15, 2011, which is incorporated herein by reference in its entirety.

FIELD

The present disclosure relates generally to apparatus and methods for particle separation and measurement. More particularly, the present disclosure relates to apparatus and methods that separate a heterogeneous mixture of particles, using one or more physical characteristics of the particles, and to apparatus and methods for measuring physical characteristics of particles.

BACKGROUND

Many applications require individual populations of cells to be separated from heterogenous samples, for example the isolation of fetal cells from maternal blood, blood cell fractionation, or the separation of circulating tumour cells from the peripheral blood of cancer patients.

Chemical separation methods based on affinity capture of cell surface molecules are very effective at isolating cells with known chemical markers, but may alter the properties of the cells. Where the components of the sample need to be preserved in their original state, chemical methods are generally undesirable. Affinity capture methods are generally not possible where no unique biomarker is known.

The separation of cells based on their physical differences is important in many areas of medical research and clinical practice. Previous technologies for physical separation include dielectrophoresis (DEP), hydrodynamic chromatography, which separate cells based on size alone, and filtration, which separate cells based on size and rigidity. Separation based on size and rigidity is generally considered to be more useful since size alone is often insufficient to distinguish different cell types. These physical sorting methods sort cell populations on the basis of physical properties such as conductivity, size, deformability or combinations thereof. A recurring limitation in the filtration of cells is clogging, or the build up of particles within the filter microstructure. Clogging alters the hydrodynamic resistance of the filter, causing loss of specificity, yield, and throughput. Additionally, constant contact between the cell membrane and the filter wall can increase the incidence of cells adsorbing on to the filter wall and, in turn, prevent the recovery of cells after separation.

In applications where the target cell population is present at a very low concentration, cell sorting methods that allow for efficient separation and recovery of cells while avoiding clogging of filters, exposure cells to excessive pressures, with very high efficiency and purity are particularly desirable.

Previous micro-scale ratchet mechanisms utilize a periodic structure having local asymmetry and local excitation to modify the motion of individual particles against the viscous drag of the particle's carrier fluid (Astumian, R. D., *Thermodynamics and kinetics of a Brownian motor*. Science, 1997. 276(5314): p. 917-922; Julicher, F., A. Ajdari, and J. Prost, *Modeling molecular motors*. Reviews of Modern Physics, 1997. 69(4): p. 1269-1281). Typically, microscale ratchet mechanisms exploit asymmetries of a flow on the basis of electrical potential (Bader, J. S., et al., *DNA transport by a micromachined Brownian ratchet device*. PNAS, 1999. 96(23): p. 13165-13169), dielectrophoresis (Gorre-Talini, L., J. P. Spatz, and P. Silberzan, *Dielectrophoretic ratchets*. Chaos, 1998. 8(3): p. 650-656; Rousselet, J., et al., *Directional Motion of Brownian Particles Induced by a Periodic Asymmetric Potential*. Nature, 1994. 370 (6489): p. 446-448), optical traps (Faucheux, L. P., et al., *Optical Thermal Ratchet*. Physical Review Letters, 1995. 74(9): p. 1504-1507), geometrical constraint imposed by obstacles (Loutherback, K., et al., *Deterministic Microfluidic Ratchet*. Physical Review Letters, 2009. 102(4): p. 045301; Matthias, S. and F. Muller, *Asymmetric pores in a silicon membrane acting as massively parallel brownian ratchets*. Nature, 2003. 424(6944): p. 53-57), and bacteria and cell motility (Galajda, P., et al., *Funnel ratchets in biology at low Reynolds number: choanotaxis*. Journal of Modern Optics, 2008. 55(19-20): p. 3413-3422; Hulme, S. E., et al., *Using ratchets and sorters to fractionate motile cells of Escherichia coli by length*. Lab on a Chip, 2008. 8(11): p. 1888-1895; Mahmud, G., et al., *Directing cell motions on micropatterned ratchets*. Nature Physics, 2009. 5(8): p. 606-612). The asymmetries in a flow correlate with particle size, and as such, are useful for size-based separation (Davis, J. A., et al., *Deterministic hydrodynamics: Taking blood apart*. Proc. Natl. Acad. Sci. U.S.A., 2006. 103(40): p. 14779-14784).

It is, therefore, desirable to provide improved apparatus and methods for particle separation.

SUMMARY

It is an object of the present disclosure to obviate or mitigate at least one disadvantage of the prior art.

In one aspect, the present disclosure provides an apparatus comprising a flow channel having a first end and a second end, a fluid flow controller for causing a carrier fluid in the flow channel to alternate between flowing in a forward direction from the first end to the second end and flowing in a reverse direction from the second end to the first end, and a microstructure within the flow channel. The microstructure comprises one or more passages therein sized to deform particles in a carrier fluid in the flow channel as the particles pass through the microstructure, and configured such that less force is required to deform particles passing through the microstructure in the forward direction than to deform particles passing through the microstructure in the reverse direction.

In another aspect, the present disclosure provides a method comprising providing a microstructure within a flow channel, the microstructure having a first side closer to a first end of the flow channel and a second side closer to a second end of the flow channel, the microstructure comprising one or more passages therein sized to deform particles in a carrier fluid in the flow channel as the particles pass through the microstructure, configured such that less force is required to deform particles passing from the first side of the microstructure to the second side of the microstructure than to deform particles passing from the second side of the microstructure to the first side of the microstructure, and forcing the carrier fluid to alternate between flowing in a forward direction from the first end to the second end and flowing in a reverse direction from the second end to the first end.

In another aspect, the present disclosure provides an apparatus for measuring particle deformability comprising an encapsulated flow channel for receiving a test particle having a size within a predetermined size range, a microfabricated constriction within the encapsulated flow channel, the constriction sized such that particles within the predetermined size range are deformed when passing through the constriction, and, a controllable pressure source in fluid communication with the encapsulated flow channel for selectively providing a controllable pressure across the constriction.

In another aspect, the present disclosure provides an apparatus for measuring particle deformability, comprising a flow channel filled with carrier fluid having a first end and a second end, the flow channel configured to permit substantially unimpeded passage of particles of a first size, a constriction in the flow channel between the first end and the second end, the constriction configured such that particles of the first size are deformed by passing therethrough, a sample inlet for introducing a test particle of the first size to the first end of the flow channel, a pressure source for selectively applying a pressure gradient to the carrier fluid in the flow channel from the first end to the second end, and a controller configured to increase the pressure gradient until the test particle is forced through the constriction and output the pressure required to forced the particle through the constriction.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1 is an apparatus for particle separation according to one embodiment of the invention.

FIG. 1A illustrates a tapered microstructure passage of an apparatus for particle separation according to another embodiment.

FIG. 1B illustrates a tapered microstructure passage of an apparatus for particle separation according to another embodiment.

FIG. 1C illustrates a tapered microstructure passage of an apparatus for particle separation according to another embodiment.

FIG. 7A illustrates an apparatus according to another embodiment of the invention.

FIG. 7B shows the arrays of obstructions in the separation chamber of the apparatus of FIG. 7A.

FIG. 7C is an enlarged view of the area indicated by box C in FIG. 7B.

FIG. 8A shows distribution of a mixed sample with PBMCs (peripheral blood mononucleocytes) demonstrating a distribution peak at a funnel size of 6 μm and MLCs (mouse lymphoma cells) demonstrating a distribution peak at about 9 μm.

FIG. 8B is a brightfield micrograph of mixed distribution with PBMCs circled in red.

FIG. 8C is a fluorescent micrograph of mixed distribution.

FIG. 8D is a bar graph illustrating separation efficiency. Cells were separated with an applied pressure of 6.9 kPa, with a forward oscillation time of 1 second, and a reverse time of 3 seconds for 1 minute of oscillation.

DETAILED DESCRIPTION

Figure 2:
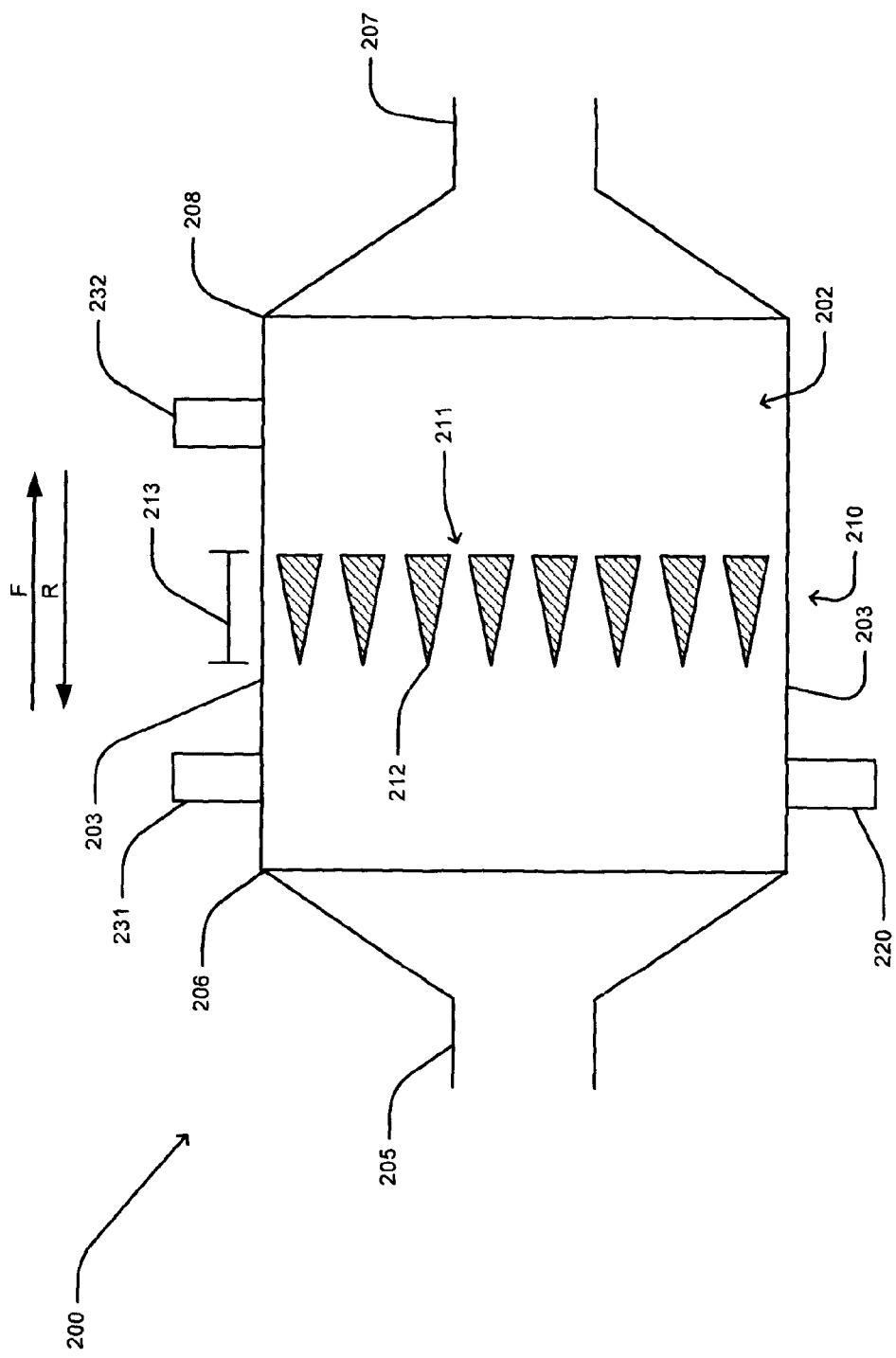
FIG. 2 is an apparatus for particle separation according to another embodiment of the invention.

Generally, the present disclosure provides methods, apparatus and systems for separation of particles based on physical properties of the particles, and methods, apparatus and systems for measuring physical properties of the particles.

Certain aspects of the invention provide, in part, methods and apparatus for particle separation. More particularly, methods and apparatus for separation of particles based on physical characteristics such as size, rigidity, or size and rigidity.

In the description that follows, a number of terms are used extensively and definitions are provided herein to facilitate understanding of various aspects of the invention. Use of examples in the specification, including examples of terms, is for illustrative purposes only and is not intended to limit the scope and meaning of the embodiments of the invention herein.

A particle may be any discrete material which can be flowed through a microscale system. Example particles include beads, cells and the like.

A heterogeneous mixture of a flow of particles may comprise at least two or more types of particles or species of particles or populations of particles. The types or species or populations of particles may differ in size, rigidity, or both size and rigidity. Additionally, one or more of the particles may comprise a selectable marker, or an identifiable marker.

Particles may be suspended in any suitable fluid, including carrier fluid, buffer, saline, water, culture medium, blood, plasma, serum, cell or tissue extract, urine or the like, or a combination thereof. As has been described in the art, a variety of techniques have been attempted to facilitate such separation, however drawbacks to each have been illustrated.

The development of microfluidics and multi-layer soft lithography have made possible the creation of a variety of microstructures and devices that function as micrometer-scale valves and pumps. It is to be understood a microstructure is a structure comprising features where one or more dimensions measure less than about 1 mm. A microfluidic device refers to a micro scale device that handles volumes of liquid on the order of nanoliters or picoliters.

In some embodiments, microfluidic devices may, for example, be constructed on chips or the like, with microstructures formed in polymer layers on a substrate. For example, some embodiments comprise microfluidic devices having a flow layer and a control layer, as described further below. In some embodiments, the flow layer has a substantially constant height, which may be selected based on the sizes of the particles of interest.

Under "laminar" flow conditions, a fluid flows through a channel without turbulence. The quantification of laminar or nonturbulent behavior is typically done through calculation of the Reynolds number, $Re = pvD/l$, where p is the fluid density, l is the fluid viscosity, v is the fluid velocity, and D is some characteristic channel dimension (typically the channel width). If the Reynolds number is small ($<1$) for typical channel geometries, then flow is laminar, reversible, and non-turbulent. For this reason, the dimensions of the channel (e.g. cross-sectional area) can be designed to account for the intended fluid properties and fluid velocity, or, equivalently, the fluid velocity can be determined by the fluid properties and the channel diameter.

Described herein are example embodiments of microscale ratchet mechanisms where the local asymmetry is coupled to the deformability of individual cells through micro-scale constrictions. In some embodiments, the constrictions are "tapered" or "funnel" shaped. For example, in some embodiments, a funnel constriction may be formed by a pair of triangular-shaped obstacles (see, for example, FIGS. 3A and 3B). Compressing cells through this constriction along the direction of the taper ("forward" direction, F) requires a smaller applied pressure than against the taper ("reverse" direction, R). Therefore, applying an unbiased pressure oscillation with amplitude above the necessary forward threshold pressure enables rectified transport along the direction of the taper.

A ratchet refers to a device or apparatus that allows migration, or net movement, in only one direction, and prevents movement in a second or opposite direction. A microfluidic ratchet is an apparatus configured to permit net particle migration in one direction (a forward direction) while preventing net particle migration in a second direction (a reverse direction). The directional movement may be facilitated by one or more obstacles configured to permit unidirectional, or net unidirectional movement of particles, oscillating flow with greater time, velocity and/or pressure in a first direction, or a combination thereof.

The threshold pressure required to deform a single cell through a micro-scale funnel constriction can be modeled by considering the cell as a liquid-filled sac with constant cortical tension (Hochmuth, R. M., *Micropipette aspiration of living cells*. Journal of Biomechanics, 2000. 33(1): p. 15-22). The end-to-end pressure required to quasi-statically form the leading and trailing surfaces in the constriction is determined by an application of the Young-Laplace law and gives equation (1):

$$\Delta P = T_C \left( \frac{1}{R_a} - \frac{1}{R_b} \right) \qquad (1)$$

where $\Delta P$ is the pressure difference across the constriction, $T_C$ is the cortical tension of the membrane (assumed to be isotropic and constant), and $R_a$ and $R_b$ are the radii of the leading and the trailing surfaces respectively. As the leading edge of the cell is pulled into the constriction, $\Delta P$ eventually reaches a maximum and then decreases upon further deformation. This phenomenon causes an instability known as a Haines jump, whereby the entire cell is pulled rapidly into the microstructure (Haines, W. B., *Studies in the physical properties of soil V The hysteresis effect in capillary properties, and the modes of moisture distribution associated therewith*. Journal of Agricultural Science, 1930. 20: p. 97-116). Since $R_b \gg R_a$, the Haines jump instability occurs near $R_a = W_0/2$ (see FIGS. 3A and 3B), while the corresponding value of $R_b$ can be determined from volume conservation. The required pressure asymmetry between deforming cells in the forward and reverse directions arises from the geometrical constraints imposed by the microstructure. Specifically, when cells are deformed in the forward direction, the presence of the funnel sidewalls reduces the value of $R_b$ and therefore requires a smaller ΔP value to reach the condition for a Haines jump as compared to when cells are deformed in the reverse direction.

This force asymmetry allows for controlled oscillatory flow and enables unidirectional (net-unidirectional) transport of particles through the constrictions, and as described infra, through an array.

Example Separation Devices

FIG. 1 schematically illustrates an example apparatus 100 according to one embodiment. Apparatus 100 comprises a flow channel 102 in fluid communication with a fluid flow controller 104. Fluid flow controller is operable to selectively cause a carrier fluid in flow channel 102 to alternate between flowing in a forward direction F from a first end 106 of flow channel 102 to a second end 108 of flow channel 102, and in a reverse direction R from second end 108 to first end 106 of flow channel. Fluid flow controller 104 may comprise, for example, one or more controllable pressure sources for urging carrier fluid to flow in either direction in channel 102. One or more pressure control structures and other elements for affecting the flow of fluid to channel 102 may also be provided, such as, for example pressure attenuators, extended microfluidic channels, valves, fluidic multiplexers, perfusion chambers, or the like.

A microstructure 110 is positioned within the flow channel 102 between first and second ends 106 and 108. Microstructure 110 comprises a passage 111 sized to deform particles in the carrier fluid as the particles pass through passage 111, and tapered such that less pressure is required to force a particle through passage 111 in the forward direction F than in the reverse direction R. In some embodiments, passage 111 is sized such that the ratio of the cross-sectional area of the particle and the cross-sectional area of the passage is between about 2.2 and about 4.5. As used herein, the term "tapered" (and derivatives thereof) in connection with a passage, pore, funnel, or the like, refers to an opening through a body which is larger on one side of the body and smaller on the other side of the body. Similarly, the expression "tapered in the forward direction" refers to an opening whose size decreases as one traverses the opening in the forward direction.

In the FIG. 1 embodiment, passage 111 is formed between a pair of obstacles on either side of the flow channel 102 having opposed angled surfaces 112 and 114. Surfaces 112 and 114 are sometimes referred to as forming a "funnel". Surfaces 112 and 114 may be substantially flat in some embodiments. Surfaces 112 and 114 may be oriented at an angle of greater than 0 degrees to about 60 degrees to each other in some embodiments (e.g., the funnel has a half angle of greater than 0 degrees to about 30 degrees). In some embodiments, surfaces 112 and 114 are oriented at an angle of about 2 degrees to each other (e.g. the funnel has a half angle of about 1 degree). In some embodiments, surfaces 112 and 114 are oriented at an angle of about 10 degrees to each other (e.g. the funnel has a half angle of about 5 degrees). In some embodiments, surfaces 112 and 114 are oriented at an angle of about 20 degrees to each other (e.g. the funnel has a half angle of about 10 degrees).

FIGS. 1A-C show microstructures 110A-110C according to other embodiments. Microstructure 110A of FIG. 1A comprises a passage 111A formed between a pair of obstacles on either side of the flow channel 102 having opposed stepped surfaces 112A and 114A. Microstructure 110B of FIG. 1B comprises a passage 111B formed between a pair of obstacles on either side of the flow channel 102 having opposed curved surfaces 112B and 114B. Microstructure 110C of FIG. 1C comprises a pair of passages 111C formed on either side of a single obstacle 113 located at approximately the centre of the flow channel 102, whereby the shape of obstacle 113 provides the desired tapering of passages 111C.

FIG. 2 shows an apparatus 200 according to another embodiment. In apparatus 200, the flow channel comprises a separation chamber 202 having first and second ends 206 and 208 and opposed sidewalls 203. Although chamber 202 is depicted as generally rectangular in the illustrated example, this is not required in all embodiments. A fluid flow controller (not shown in FIG. 2) distributes carrier fluid into separation chamber 202 at the first and second ends 206 and 208 thereof through one or more carrier fluid channels 205 and 207, respectively, to cause the carrier fluid to alternate between flowing in the forward F and reverse R directions. Filter barriers (not shown in FIG. 2) may be provided at either end of chamber 202 to prevent particles in chamber 202 from entering carrier fluid channels 205 and 207. A microstructure comprising an array 210 of obstacles 212 is disposed within separation chamber 202. Passages 211 are formed between adjacent obstacles 212. The opening width (or pore size, $W_0$, see FIGS. 3A and 3B) of passages 211 is selected to be smaller than the size of particles to be separated, such that the particles are deformed as they are travel through passages 211. The length 213 of passages 211 is determined by the length of obstacles 212. A sample inlet 220 is positioned to introduce a sample of particles suspended in carrier fluid into chamber 202 between first end 206 and array 210. First and second sample outlets 231 and 232 are positioned on either side of array 210 for removing separated particles from chamber 202. Inlet 220 and outlets 231, 232 may be opened and closed by means of suitable valves.

In operation, inlet 220 is opened to allow a sample of particles into chamber 202, then inlet is closed and the carrier fluid is oscillated within chamber 202 by alternately providing pressurized carrier fluid from carrier fluid channels 205 and 207. The applied pressures (forward and reverse) are selected based on expected threshold pressures to force the particles through passages 211. For example, the forward pressure may be selected to be greater than the threshold pressure to force a particle through one of the passages 211 in the forward direction, and the reverse pressure may be selected to be less than the threshold pressure to force a particle through one of the passages in the reverse direction such that the particle is prevented from transiting through a passage in the reverse direction. Oscillation of the carrier fluid causes deformable particles to accumulate between the array 210 and the second end 208, while more rigid particles accumulate between the array 210 and the first end 206. The deformable particles which have passed through array 210 are removed through outlet 232 and the more rigid particles which have not passed through array 210 are removed through outlet 231. In some embodiments, additional inlets (not shown in FIG. 2, see FIG. 2A and FIG. 7) may be provided for introducing additional carrier fluid for flushing particles out outlets 231 and 232 after separation.

Figure 2A:
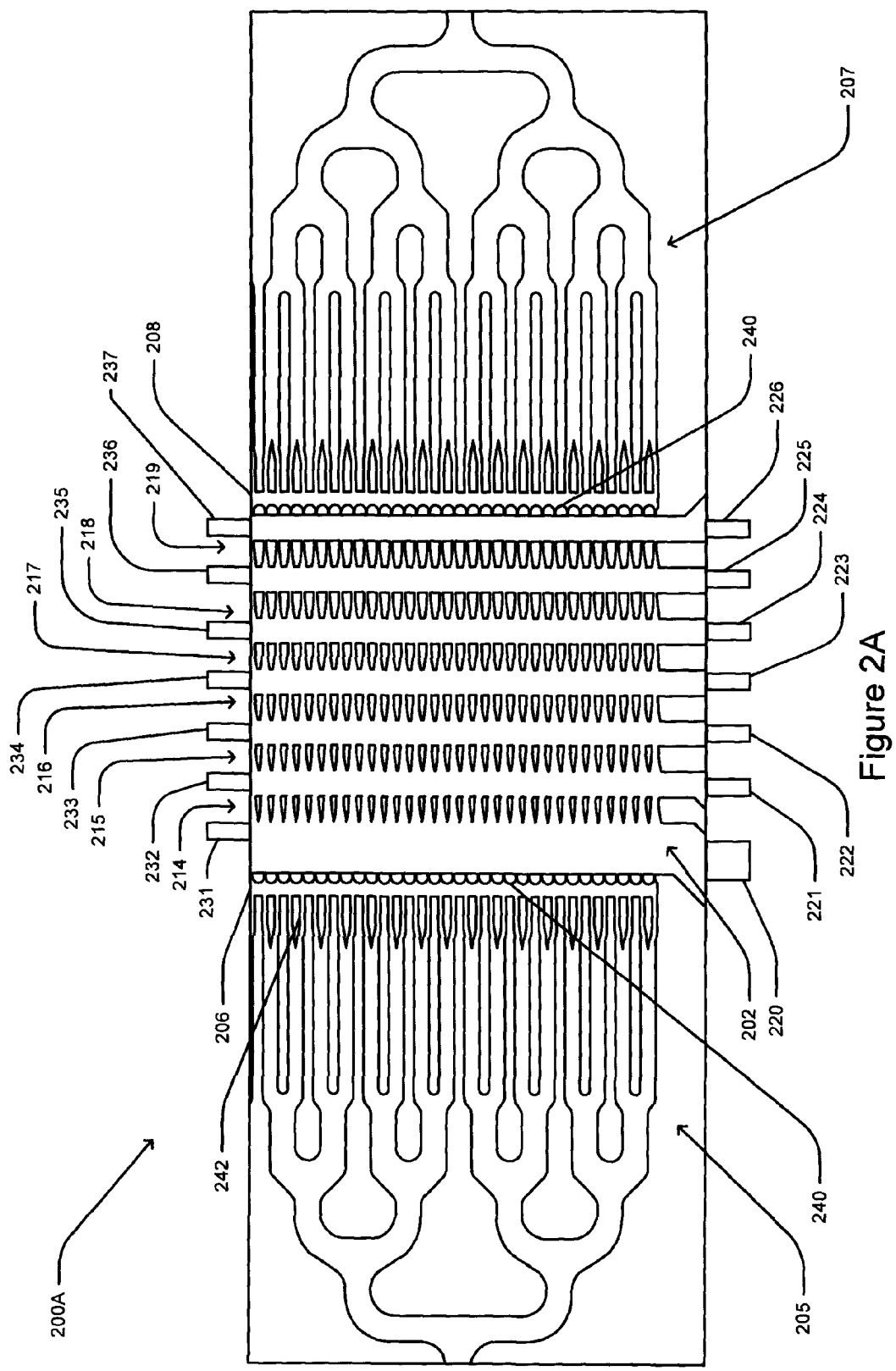
FIG. 2A is an apparatus for particle separation according to another embodiment of the invention.

FIG. 2A shows an apparatus 200A according to another embodiment. Apparatus 200A has a number of elements in common with apparatus 200 of FIG. 2, which are identified with corresponding reference numbers and will not be described again. Apparatus 200A comprises six arrays of obstacles, namely arrays 214, 215, 216, 217, 218 and 219. Each of arrays 214-219 has the same number of obstacles, but the size of the obstacles increases in each successive array moving forward through separation chamber 202, such that the size of the passages between obstacles is decreased with each successive array, as fluid and particles progress through the chamber 202 in the forward direction F. Fluid flowing through the separation chamber 202 flows around and between the obstacles, the obstacles extending across the flow channel, being either fixed to, integral with or abutting the top and bottom surfaces of the flow channel. Apparatus 200A also comprises seven outlets 231, 232, 233, 234, 235, 236 and 237 for removing separated particles from respective areas of chamber 202, and six additional inlets 221, 222, 223, 224, 225 and 226 (in addition to sample inlet 220) for flushing separated particles out of outlets 231-237.

Apparatus 200A also comprises an optional filter barrier 240 near each of the first and second ends 206 and 208 of chamber 202. Before interacting with the arrays of obstacles, the fluid flows around and between filter barrier 240. Each filter barrier 240 comprises a plurality of obstacles (filter-barrier obstacles) having a flat side facing the one or more arrays therein. In the embodiment illustrated in FIG. 2A, the filter barrier obstacles are substantially semi-circular in cross-section, with a rounded side facing the carrier fluid channels 205, 207. Obstacles of the filter barrier 240 extend across the flow channel, being either fixed to, integral with or abutting the top and bottom surfaces of the flow channel. In the illustrated example, the filter-barrier obstacles are all of a same or similar size, and have a spacing, or gap, between adjacent filter-barrier obstacles which is small enough to prevent particles in chamber 202 from passing filter barriers 240. It is to be understood that filter barriers 240 are not required in all embodiments. For example, in some embodiments particles may be permitted to carrier fluid channels 205, 207 at either or both ends of apparatus 200A, or the individual channels of carrier fluid channels 205, 207 themselves may be small enough to prevent particles from entering. While semi-circular-shaped filter-barrier obstacles are illustrated in the example of FIG. 2A, it is to be understood that filter-barrier obstacles may be of any shape including teardrop-shape, posts, cup-shaped structures, V-shaped structures, trapezoid, funnel-shaped, square, round, elliptical, or other shapes. Corners of obstacles may be 'sharp' or may be rounded; an obstacle may have a combination of corner configurations.

In the example apparatus 200A shown in FIG. 2A, carrier fluid channels 205 and 207 at the ends of apparatus 200A each comprise a distribution network having a plurality of subchannels 242 in fluid communication with the chamber 202. Without wishing to be bound by theory, the subchannels 242, by dispersing the fluid flow through multiple subchannel inlets when entering the separation chamber 202 provide for a more uniform velocity profile within the separation chamber 202, relative to a single inlet (which may provide a more parabolic velocity profile, where the fluid velocity along a longitudinal axis of the chamber 202 may be substantially greater than that along the sides of the chamber). In the example illustrated in FIG. 2A, the number of subchannels 242 is the same as the number of passages between obstacles in arrays 214-219, which is also the same number of gaps in filter barriers 240. Also, in the illustrated example, the subchannels 242, the gaps in filter barriers 240 and the passages between obstacles in arrays 214-219 are all aligned.

Apparatus such as example apparatuses 200 and 200A may further comprise, or be in fluid communication with, and operationally linked to, one or more pumps, valves, fluid and/or sample reservoirs as are known in the art.

Figure 4:
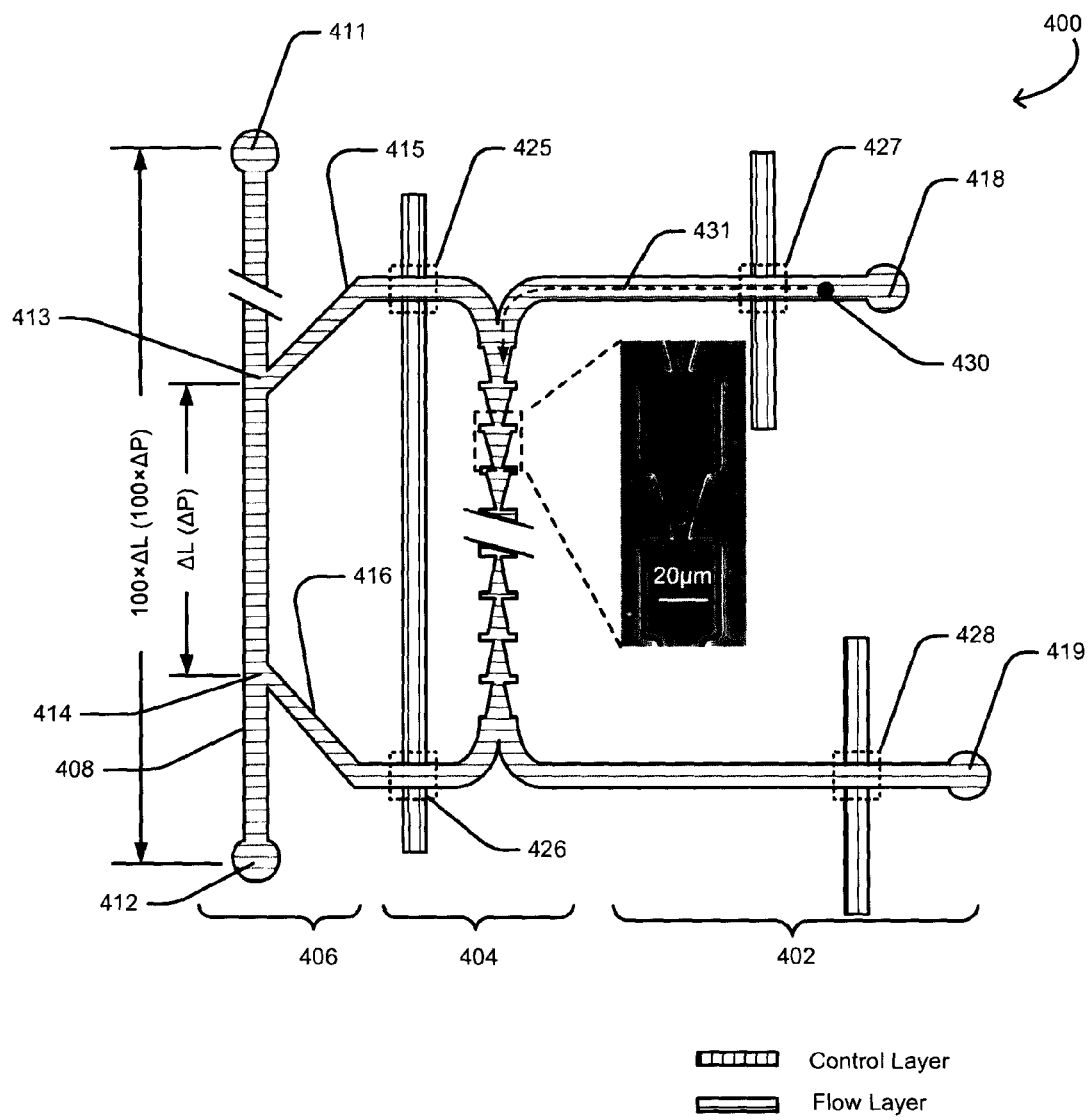
FIG. 4 shows a design of a two-layer microfluidic device for measuring the pressure required to deform single cells through micro-scale funnel constrictions according to one embodiment.

Obstacles of arrays in the separation chamber may be of any suitable shape or configuration—the triangular obstacles shown in FIG. 2, or the rounded triangles and trapezoids shown in FIG. 2A are only examples. Other examples include teardrop-shape, posts, cup-shaped structures, V-shaped structures, trapezoid, funnel-shaped, square, round, parabolic, hemispherical, elliptical, or other shapes. Corners of obstacles may be 'sharp' or may be rounded; an obstacle may have a combination of corner configurations. In some embodiments, an obstacle with a tapered shape, such as a triangle, trapezoid or teardrop may be suitable. The orientation of the narrow end of the obstacle with a tapered shape may be toward the first end of the flow channel; positioning of tapered obstacles adjacent to one another in the array provides for a funnel-shape formed therebetween. In some embodiments, one or more of the obstacles within an array may be continuous with, or formed from, a side wall of the flow chamber. FIG. 4, which is described in further detail below, illustrates a particular embodiment where an array of two obstacles, each continuous with a side wall of the flow channel form a funnel between them; the illustrated configuration in FIG. 4 provides for a plurality of arrays, each array may be described as comprising two obstacles, or one funnel.

Figure 3A:
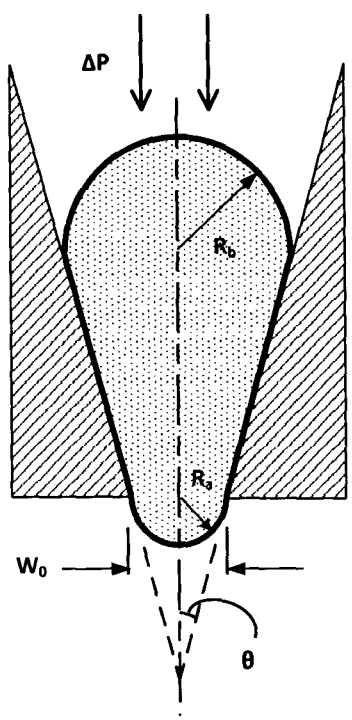
FIGS. 3A and 3B show a schematic deformation of a single cell through micro-scale funnel constrictions in forward and reverse directions, respectively. Parameters of the microstructure include the funnel pore size ($W_0$) and half-angle of the funnel taper ($\theta$).
Figure 3B:
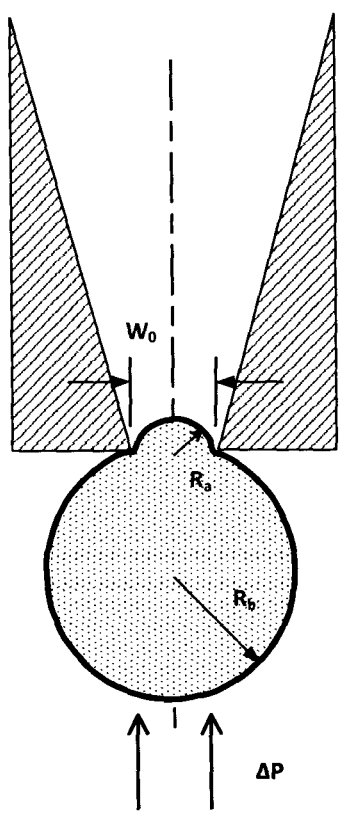

The passages between obstacles of an array may be described by the pore size ($W_0$) (e.g., the width of the passage at the narrowest point of the passage) and the half-angle of the funnel taper ($\theta$), as illustrated schematically in FIGS. 3A and 3B. In some embodiments, the array of obstacles are of a size and position to provide an array of funnel-shaped passages therebetween. The pore size—$W_0$—may be selected depending on the size range of the particles in the sample, and the desired separation. The funnel-shaped passages may be parabolic or tapered, with concave, convex, convergent or divergent, stepped, or straight sides, at an angle defined by the half-angle of the funnel taper $\theta$. $W_0$ may be any suitable value from about 1 to about 20 μm, or any amount therebetween, for example 1, 2, 3, 4, 5, 6, 7, 8, 9, 10, 11, 12, 13, 14, 15, 16, 17, 18, 19 or 20 μm, or any amount therebetween. The half-angle of the funnel taper 9 may be any suitable value from about 1 to about 30 degrees, or any amount therebetween; for example 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees, or any amount therebetween. In some embodiments, the half-angle of the funnel is 5 degrees. In some embodiments, the half-angle of the funnel is 10 degrees. The length of the funnel (element 213 in FIG. 2) is dependent on the length of the obstacles forming the passage, and may be from about 10 to about 100 μm, or any amount therebetween, for example 10, 20, 30, 40, 50, 60, 70, 80, 90 or 100 μm, or any amount therebetween. In embodiments with multiple arrays, arrays of obstacles may be separated by any suitable distance, for example from about 20 to about 200 μm, or any amount therebetween, for example about 20, 30, 40, 50, 60, 70, 80, 90, 100, 110, 120, 130, 140, 150, 160, 170, 180, 190 or 200 μm, or any amount therebetween. The distance separating the arrays may be selected based on the volume or quantity of particles to be separated. The arrays may be spaced apart by different distances, or may all be spaced apart by the same distance.

Any number of arrays may be used within a separation chamber, selection of a suitable number will be within the ability of one skilled in the art, and dependent, in part, on the volume of sample, quantity of particles within a sample, and the number of different sizes or types of particles within a sample. For example, a separation chamber may have from about 1 to about 20 arrays, or any amount therebetween, for example, 1, 2, 3, 4, 5, 6, 7, 8, 9, 10, 11, 12, 13, 14, 15, 16, 17, 18, 19 or 20. In some embodiments, the number of outlets from the separation chamber may be one greater than the number of arrays.

In some embodiments, extended microfluidic channels between, and in fluid communication with, one or more pumps or other pressure sources and the flow channel provide extra hydrodynamic resistance to allow for more precise control of flow through device when flow is controlled from a standard pressure source (see, for example, FIG. 7, discussed below). Without wishing to be bound by theory, fluid flow in a microfluidic system may be considered to be analogous to electrical circuits where the flow rate is equivalent to electrical current, pressure is equivalent to voltage, and hydrodynamic resistance is equivalent to electrical resistance. In some embodiments, a selected hydrodynamic resistance may be calculated based on a selected fluid velocity of 100 μm/s in the sorting area, at a selected pressure of 5 kPa. In some embodiments, the selected flow rate and pressure are design constraints, and, the necessary hydrodynamic resistance is found using the formula:

$$R_H = \frac{\Delta P}{Q} \quad (2)$$

Where $R_H$ is the hydrodynamic resistance, $\Delta P$ the pressure drop, and Q the volumetric flow rate. For flow within a rectangular channel, the flow rate can be represented by:

$$Q = Uwh \quad (3)$$

The width of the channel is w, and the height of the channel is h, while U is the velocity of the flow. For a rectangular channel in laminar flow with h>w, the hydrodynamic resistance can be calculated using:

$$R_H \approx \frac{12\mu L}{wh^3} \quad (4)$$

Where L is the length of the channel and the viscosity μ of water is $10^{-3}$ Pa s. The hydrodynamic resistance of the sorting area was assumed to be negligible in comparison to the resistance contribution from the additional channel length, so the total channel length needed was calculated based on the total amount of resistance needed.

The carrier fluid may be any fluid that is compatible with both the polymer comprising the apparatus, and the particles to be separated or sorted. Where the particles are cells, the carrier fluid is generally an isotonic, aqueous solution with a pH from about 3 to about 10, or a pH from about 3, 4, 5, 6, 7, 8 or 9 to about 4, 5, 6, 7, 8, 9 or 10, or any amount therebetween. More particularly, the carrier fluid may have a pH from about 6.5 to 8.0, or any amount therebetween. The carrier fluid may be a buffer, for example phosphate buffered saline (PBS), Dulbecco's PBS, bicarbonate buffer, Tris, tricine, TAPS, HEPES, MOPS, PIPES, MES, SSC, Cacodylate or the like, or other biologically-compatible buffers as are known in the art. Where such a buffer needs to be prepared, one of skill in the art will be aware of standard reference documents that outline the necessary reagents, quantities, pH and other aspects necessary for proper handling. In some embodiments, the carrier fluid may be isotonic saline. The carrier fluid may further comprise a surfactant, such as a biologically compatible surfactant.

FIG. 7A shows an apparatus 700 according to another example embodiment. Apparatus 700 comprises a separation chamber 702 having a first end 706 and a second end 708. A first end carrier fluid control system 710 provides carrier fluid to first end 706 for generating flow in a forward direction F through chamber 702, and a second end carrier fluid control system 720 provides carrier fluid to second end 708 for generating flow in a reverse direction R through chamber 702.

First end carrier fluid control system 710 comprises a forward pressure inlet channel 712 (which may be an extended serpentine microfluidic channel to provide additional hydrodynamic resistance) coupled to a pressure source (not shown). Forward pressure inlet channel 712 is in fluid communication with a first end distribution network 714 through a forward supply valve 713. Network 714 is also in fluid communication with an oscillation outlet 716 through an oscillation outlet valve 715. Oscillation outlet 716 provides a path for carrier fluid to leave chamber 702 during reverse flow, and may be in fluid communication with a reservoir or the like (not shown) for receiving carrier fluid. Similarly, second end carrier fluid control system 720 comprises a reverse pressure inlet channel 722 (which may be an extended serpentine microfluidic channel to provide additional hydrodynamic resistance) coupled to a pressure source (not shown). Reverse pressure inlet channel 722 is in fluid communication with a second end distribution network 724 through a reverse supply valve 723. Network 724 is also in fluid communication with an oscillation outlet 726 through an oscillation outlet valve 725. Oscillation outlet 726 provides a path for carrier fluid to leave chamber 702 during forward flow, and may be in fluid communication with a reservoir or the like (not shown) for receiving carrier fluid. First and second end distribution networks 714 and 724 are in fluid communication with first end subchannels 718 and second end subchannels 728, respectively (see FIG. 7B) for introducing carrier fluid into chamber 702.

Apparatus 700 also comprises an inlet system 730 and an outlet system 740 on opposite sides of chamber 702. Inlet system 730 comprises a sample inlet 732 for introducing a sample of particles into chamber 702 near first end 706, and a flush fluid supply channel 734 in fluid communication with a plurality of additional inlets 736 for supplying carrier fluid to flush particles from chamber 702 after separation. An inlet valve 738 is operable to selectively open and close the connection between inlets 732, 736 and chamber 702. Outlet system 740 comprises a plurality of outlets 741-747 for removing particles from chamber 702. An outlet valve 748 is operable to selectively open and close the connection between outlets 741-747 and chamber 702.

FIG. 7B shows an example of the microstructure within chamber 702. A first filter barrier 751 is provided near first end 706 of chamber 702 for preventing particles in chamber 702 from entering subchannels 718. Likewise, a second filter barrier 752 is provided near second end 708 of chamber 702 for preventing particles in chamber 702 from entering subchannels 728. A plurality of arrays of obstacles 761-766 are provided in chamber 702 between filter barriers 751 and 752. FIG. 7C illustrates various dimensions of the microstructure, with g referring to the width of the gap between adjacent filter-barrier obstacles in filter barriers 751 and 752, $W_O$ referring to the pore size of the passages between adjacent obstacles of arrays 761-766, s referring to the distance between the centers of adjacent passages, l referring to the length of the passages and d referring to the distance between successive arrays. The passages between adjacent obstacles of arrays 761-766 become successively narrower moving forward through chamber 702 (e.g., $W_O$ is the largest for the passages of array 761, and gets smaller with each successive array 762, 763, 764, 765 and 766).

In some embodiments, the number of outlets from the separation chamber is one greater than the number of arrays of obstacles within the separation chamber. With reference to FIGS. 7A and 7B, inlets 732, 736 and outlets 741-747 may be substantially aligned with corresponding spaces between arrays 761-766 and filter barriers 751, 752. In particular, sample inlet 732 and first outlet 741 are substantially aligned with the space between first filter barrier 751 and first array 752. Likewise, one of the additional inlets 736 is substantially aligned with each of outlets 742-747, and with the spaces beyond each of arrays 761-766. Such an arrangement may facilitate flushing of separated particles from chamber 702.

Example Measurement Devices

FIG. 4 shows an example apparatus 400 for measuring the pressure difference required to deform single cells both ways through various sized funnel constrictions. Apparatus 400 comprises a control layer and a flow layer, which are indicated by vertical and horizontal fill patterns, respectively, as indicated by the legend in FIG. 4. Apparatus 400 comprises generally a cell inlet portion 402, a funnel chain portion 404 and a pressure attenuator portion 406. Funnel chain portion 404 comprises a plurality of funnel constrictions (e.g., two sets of ten funnels) arranged in opposite polarity and decreasing in pore size towards the center of the funnel chain. Cell inlet portion 402 comprises first and second cell introduction zones 418 and 419 which are in fluid communication with either end of the funnel chain through valves 427 and 428. An example cell 430 is shown after introduction at 418, and moves into the funnel chain as indicated by arrow 431. Pressure attenuator portion 406 comprises a long microchannel 408 with ends 411 and 412. Microchannel 408 is in fluid connection at points 413 and 414 with branch channels 415 and 416, respectively, which are in turn connected to either end of funnel chain through valves 425 and 426. An external pressure applied across ends 411 and 412 results in an attenuated pressure across points 413 and 414 (and thus across the funnel chain when valves 425 and 426 are open) which is a fraction of the external pressure, the fraction determined by the ratio of the distance between points 413 and 414 to the distance between points 411 and 412. In the illustrated embodiment, pressure attenuator portion 406 is configured to provide 1/100 of the applied external pressure to the funnel chain, but it is to be understood that a different fraction of external pressure may be provided in some embodiments. Also, in some embodiments, pressure attenuator portion 406 may be omitted (e.g., if a sufficiently finely controllable external pressure source is provided). Details of operation of apparatus 400 and example experiments are described below under the heading Example 4.

Figure 4A:
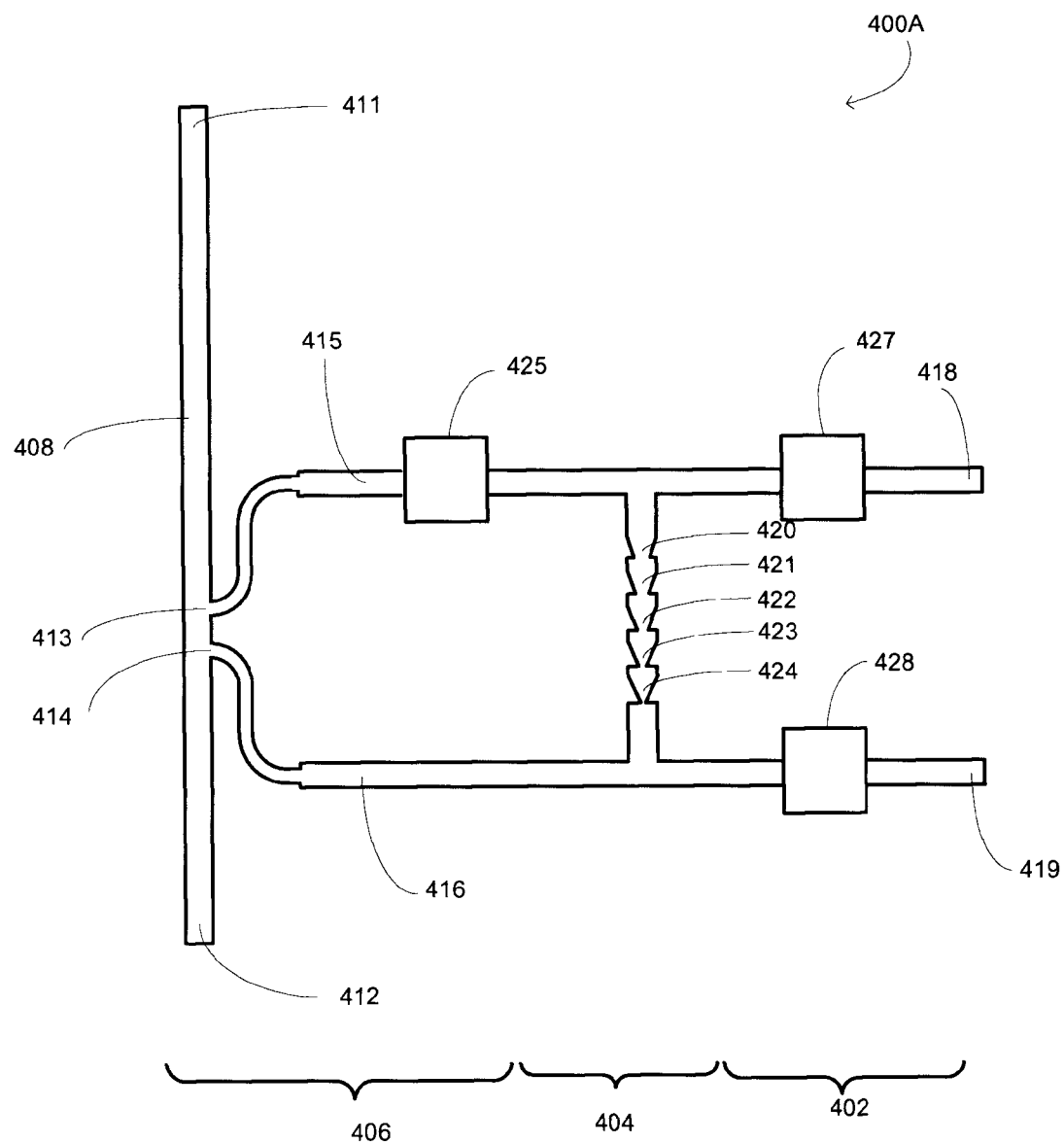
FIG. 4A shows an example microfluidic device for measuring the pressure required to deform single cells through micro-scale funnel constrictions according to another embodiment.

FIG. 4A shows an example apparatus 400A according to another embodiment. Apparatus 400A has a number of elements in common with apparatus 400 of FIG. 4, which are identified with corresponding reference numbers and will not be described again. Apparatus 400A differs from apparatus 400 in that funnel chain portion 404 in apparatus 400A comprises five funnel constrictions 420, 421, 422, 423 and 424 arranged in the same polarity, and in that there is no valve in branch channel 416.

Figure 4B:
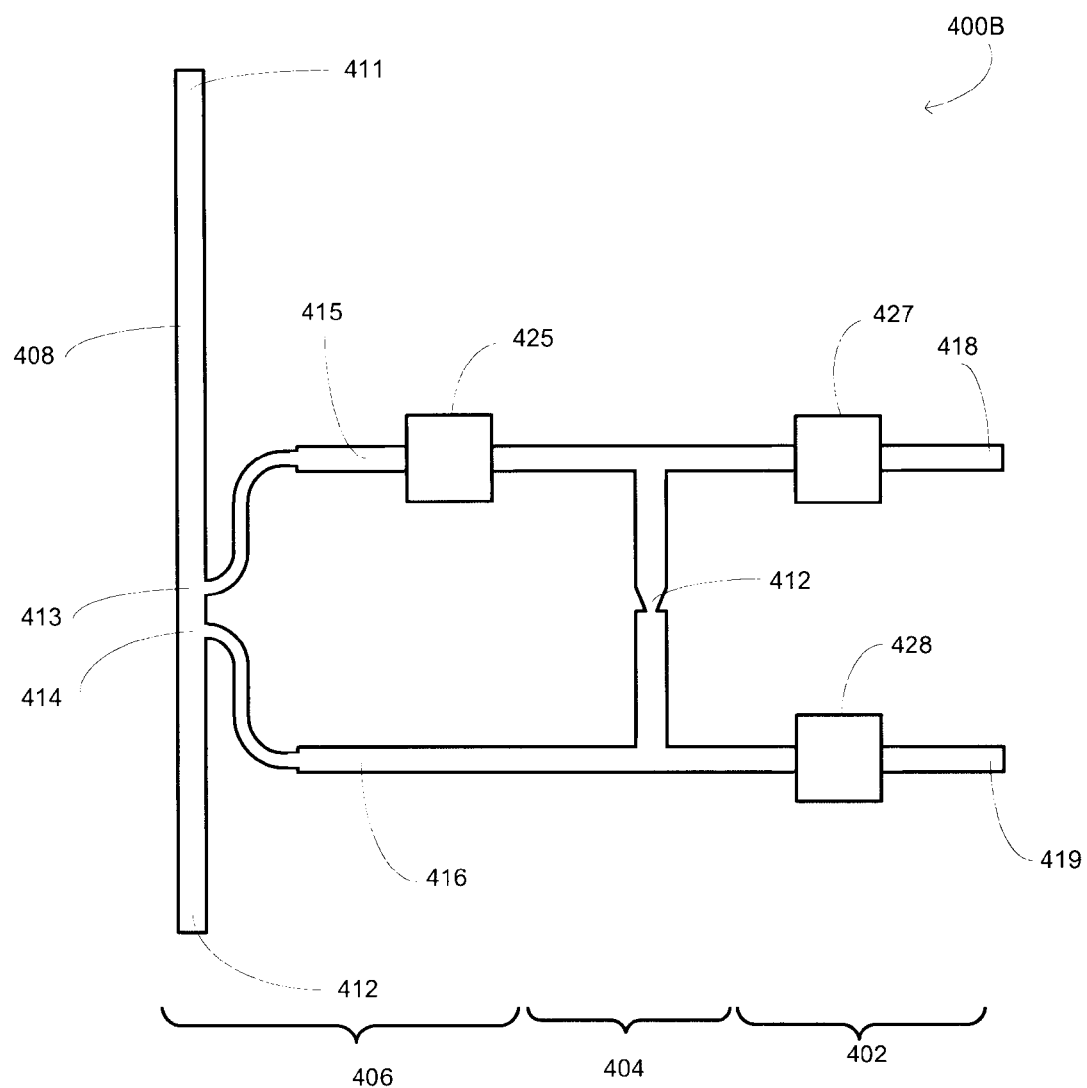
FIG. 4B shows an example microfluidic device for measuring the pressure required to deform single cells through a single micro-scale funnel constriction according to another embodiment.

FIG. 4B shows an example apparatus 400B according to another embodiment. Apparatus 400B has a number of elements in common with apparatus 400 of FIG. 4 and apparatus 400A of FIG. 4A, which are identified with corresponding reference numbers and will not be described again. Apparatus 400B is substantially the same as apparatus 400A, except that funnel chain portion 404 in apparatus 400B comprises only a single funnel constriction 412.

Apparatus such as example apparatuses 400, 400A and 400B may be operably connected to a variety of additional elements, such as, for example, pressure sources, controllers, and the like. For example, in some embodiments, apparatus 400, 400A and/or 400B may be coupled to a controllable pressure source and a controller configured to gradually increase pressure across a constriction until a particle passes through the constriction, and output the pressure required to force the particle through the constriction.

Example Applications

Where the particle is a cell, separation of one or more cell types or species from another in media, blood or other fluid has several applications. Without limitation, such applications may include leukapheresis, blood bank processing, separation of asynchronous cells in culture, enrichment of selected cell types (e.g. stem cells from cord blood or bone marrow or adipose tissue), and identification and/or enumeration of rare cell types (e.g. circulating tumor cells in the blood). Such circulating tumor cells may be of particular diagnostic, prognostic or clinical interest as markers of the development and extent of cancer and/or metastasis. Circulating tumor cells (CTC) demonstrate physical differences from other hematological cells, namely size and rigidity. These physical differences may be able to be exploited in other cell types such as white blood cells (WBCs), cardiac myocytes, mesenchymal stem cells (MSCs), and pluripotent stem cells. Additionally, it may be beneficial to separate red blood cells from other cells in a blood sample to facilitate subsequent analysis. For example, separated cells may be analyzed by polymerase chain reaction (PCR) techniques and other techniques as known in the art. Haemoglobin in RBCs is an inhibitor of the PCR reaction and thus the presence of RBCs is detrimental in PCR reactions, as is known in the art.

Cells may be obtained from, or found within, for example, cell culture, an environmental sample, a subject's body fluids, or a tissue sample. Cells may be eukaryotic cells, including plant cells. A cell culture may be included in a process for isolating, enriching, or isolating and enriching one or more particular cell types or cell species. Tissue samples may be obtained by, for example, curettage, exfoliation, tissue scraping or swabbing, needle aspiration biopsy or needle (core) biopsy, incisional biopsy for sampling tissue, or excisional biopsy, which may entail total removal of the tissue of interest. Body fluids include, for example, blood, bone marrow, plasma, serum, sputum, urine, semen, amniotic fluid, cord blood, cerebrospinal fluid or the like.

The deformability of cells is related to the composition of the cytoplasm and the structure of the cytoskeleton, and as a result, can vary by orders of magnitude depending on cell type and disease status. By coupling cell deformability with a local asymmetry to form a micro-scale ratchet, cells may be selectively transported based on differences in their internal mechanics, thus allowing for separation and/or sorting of a heterogeneous population of cells and/or particles based on morphology, which in turn may be indicative of disease status.

Cells may be obtained from, or found within, for example, cell culture, an environmental sample, a subject's body fluids, or a tissue sample. Cells may be eukaryotic cells, including plant cells. A cell culture may be included in a process for isolating, enriching, or isolating and enriching one or more particular cell types or cell species. Tissue samples may be obtained by, for example, curettage, exfoliation, tissue scraping or swabbing, needle aspiration biopsy or needle (core) biopsy, incisional biopsy for sampling tissue, or excisional biopsy, which may entail total removal of the tissue of interest. Body fluids include, for example, blood, bone marrow, plasma, serum, adipose tissue, sputum, urine, semen, amniotic fluid, cord blood, cerebrospinal fluid or the like.

An environmental sample may comprise a fluid and one or more species of particle. For example, the environmental sample may comprise fresh or salt water (e.g. seawater, lake water, water from a treatment facility, sewer outflow or other water samples) that may be acquired when monitoring a location or environment. The environmental sample may comprise soil, plant matter, or other matter that may be found when monitoring a location or environment. The environmental sample may comprise particles, such as those exemplified herein, including eukaryotic cells, and/or prokaryotic cells, and/or minerals, particulates or the like.

A subject may be an animal, such as a mammal, reptile, bird or fish; examples of mammals include a rodent, cat, dog, primate, sheep, cow, pig, horse or ferret; examples of rodents include a mouse, rat, guinea pig or hamster; examples of primates include a human, a monkey, chimpanzee, rhesus macaque or green monkey.

Examples of cells include red blood cells, white blood cells, peripheral blood mononucleocyte (PBMC), stem cells, tumor cells, cancer cells (primary or immortalized), animal or human cell lines (primary cell lines or immortalized cell lines) and the like. Examples of stem cells include adult stem cells, somatic stem cells, embryonic stem cells, non-embryonic stem cells, pluripotent stem cells, induced pluripotent stem cells, totipotent stem cells, multipotent stem cells, unipotent stem cells, hematopoetic stem cells, neural stem cells, mesenchymal stem cells, endothelial stem cells, and the like Cancer cells may be from any type of cancer or tumor. Non-limiting examples of different types of cancers and tumors include: carcinomas, such as neoplasms of the central nervous system, including glioblastoma, astrocytoma, oligodendroglia) tumors, ependymal and choroid plexus tumors, pineal tumors, neuronal tumors, medulloblastoma, schwannoma, meningioma, and meningeal sarcoma; neoplasms of the eye, including basal cell carcinoma, squamous cell carcinoma, melanoma, rhabdomyosarcoma, and retinoblastoma; neoplasms of the endocrine glands, including pituitary neoplasms, neoplasms of the thyroid, neoplasms of the adrenal cortex, neoplasms of the neuroendocrine system, neoplasms of the gastroenteropancreatic endocrine system, and neoplasms of the gonads; neoplasms of the head and neck, including head and neck cancer, neoplasms of the oral cavity, pharynx, and larynx, and odontogenic tumors; neoplasms of the thorax, including large cell lung carcinoma, small cell lung carcinoma, non-small cell lung carcinoma, malignant mesothelioma, thymomas, and primary germ cell tumors of the thorax; neoplasms of the alimentary canal, including neoplasms of the esophagus, stomach, liver, gallbladder, the exocrine pancreas, the small intestine, veriform appendix, and peritoneum, adneocarcinoma of the colon and rectum, and neoplasms of the anus; neoplasms of the genitourinary tract, including renal cell carcinoma, neoplasms of the renal pelvis, ureter, bladder, urethra, prostate, penis, testis; and female reproductive organs, including neoplasms of the vulva and vagina, cervix, adenocarcinoma of the uterine corpus, ovarian cancer, gynecologic sarcomas, and neoplasms of the breast; neoplasms of the skin, including basal cell carcinoma, squamous cell carcinoma, dermatofibrosarcoma, Merkel cell tumor, and malignant melanoma; neoplasms of the bone and soft tissue, including osteogenic sarcoma, malignant fibrous histiocytoma, chondrosarcoma, Ewing's sarcoma, primitive neuroectodermal tumor, and angiosarcoma; neoplasms of the hematopoietic system, including myelodysplastic syndromes, acute myeloid leukemia, chronic myeloid leukemia, acute lymphocytic leukemia, HTLV-I and T-cell leukemia/lymphoma, chronic lymphocytic leukemia, hairy cell leukemia, Hodgkin's disease, non-Hodgkin's lymphomas, and mast cell leukemia; and neoplasms of children, including acute lymphoblastic leukemia, acute myelocytic leukemias, neuroblastoma, bone tumors, rhabdomyosarcoma, lymphomas, renal tumors, and the like.

An apparatus according to various embodiments of the invention, a system comprising such an apparatus, or methods according to various embodiments of the invention provide cell-handling capabilities for sorting and capturing a subpopulation of cells in a format which allows for subsequent manipulation and/or analysis. Such a system may allow for selection of a single cell from a population, the capture of this cell at any position within an addressable array of chambers, the application of one or more reaction conditions, and imaging of each reaction chamber. This functionality may provide an instrument for chemical genetics studies of a plurality of single cells. Examples of cell-based microfluidic assays are described in, for example PCT Publication WO 98/00231 and WO 98/45481. Cell-based microfluidic assays may be useful for screening of binding and/or internalization of cell ligands, for example, receptor ligands, drugs, cofactors and the like.

Once separated from a heterogenous mixture a cell or cells may be subjected to further analysis, for example nucleic acid sequencing, nucleic acid amplification, protein extraction or isolation, fluorescent in situ hybridization, immunostaining, patch-clamping, calcium flux measurements, whole cell electrophoresis, or any of several methods of cell analysis known in the art. Additionally, the capture and imaging of one or a few single cells in microfabricated devices may be used to monitor cellular response to varying concentrations of one or a few chemical stimuli.

Nucleic acid may be extracted from cells separated from a heterogenous mixture, and the nucleic acid subjected to sequence analysis. Alternatively, a target nucleic acid within the cell may be specifically identified using a probe, or specifically amplified using one or more primers.

A target nucleic acid is a nucleic acid comprising one or more sequences of interest. The presence of a target nucleic acid in a sample or reaction mixture may be detected, and depending on the assay design, may also be quantified. The target nucleic acid may be DNA, for example genomic DNA, extrachromosomal DNA, mitochondrial DNA, cDNA or the like. The target nucleic acid may be RNA, for example mRNA, RNAi, miRNA, hnRNA or the like. The target nucleic acid may comprise a polymorphism.

Detection of particular cell types within a body fluid may be useful in determining the state of a pathology of a subject. For example, a subject diagnosed with a tumor may have their blood, plasma or serum periodically tested by passaging such body fluid through an apparatus according to various embodiments herein. Larger and/or more rigid cells may be subsequently analyzed for their nucleic acid complement, protein or polypeptide complement. Detection of circulating tumor cells in the blood or plasma or lymph of a subject may be indicative of an early stage of metastasis.

Examples of Operation

Reference is made to FIGS. 1, 2, 2A and 7 for the respective components of an apparatus used for separating particles according to example embodiments of the invention.

The pressure of the carrier fluid in the forward and reverse flows may be regulated by one or more pumps or similar devices to controllably push fluid through the flow chamber in a unidirectional or an oscillating manner. The carrier fluid is driven through a conduit, into an inlet and through a distribution network into the flow channel/separation chamber of the apparatus. Valves operate to contain the directionality of the flow and ensure that fluid from a reverse flow is directed via an oscillation outlet to a reservoir or similar waste storage. This allows for input of fresh carrier fluid into the separation chamber. Particles may be prevented from flowing back into the distribution network during an opposing flow cycle by a filter barrier. A sample comprising particles is placed into a separation area in the flow channel/separation chamber via a sample inlet; additional carrier fluid or buffer may be provided via the sample inlet, or one or more separate buffer inlets, at a desired rate or volume.

The sample may be introduced into the separation area before carrier fluid is introduced; alternately the separation chamber may be flushed by carrier fluid in advance of introduction of the sample.

To perform a particle separation, inlet and outlet valves are closed, and the fluid and particles within the separation area subjected to an oscillating pressure flow (oscillating fluid flow, oscillating flow of carrier fluid). The length of time of the forward flow and reverse flow may be the same, or may be different. The forward flow may be of a longer duration than the reverse flow or the reverse flow may be of a longer duration than the forward flow. The forward and reverse flow pressures are non-zero, and may be of the same pressure, or may be different. The pressure of the forward flow may be greater than the reverse flow, or the pressure of the reverse flow may be greater than the forward flow. Multiple cycles of oscillation may be performed; a cycle is one forward flow and one reverse flow, a 'rest' period where there is no pressure and no fluid flow may precede, follow, or be in-between the forward and reverse flow steps of a cycle.

The forward or reverse flow may independently be from about 0.1 to about 10 seconds in duration; or from about 0.1, 0.5, 1, 2, 3, 4, 5, 6, 7, 8, 9 or 10 seconds in duration, or any amount therebetween. The pressure of the forward or reverse flow may independently be from about 1 kPa to about 50 kPa, or any amount therebetween, for example 1, 5, 10, 15, 20, 25, 30, 35, 40, 45 or 50 kPa, or any amount therebetween. Where a 'rest' period is included in the cycle, it may be of any duration from about 0.5 to about 10 seconds in duration; or from about 0.5, 1, 2, 3, 4, 5, 6, 7, 8, 9 or 10 seconds in duration, or any amount therebetween. The number of cycles of oscillation may be from about 1 to about 20, or any amount therebetween, for example 1, 2, 3, 4, 5, 6, 7, 8, 9, 10, 11, 12, 13, 14, 15, 16, 17, 18, 19 or 20, or any amount therebetween.

Once a suitable number of cycles have been performed, the outlets may be opened simultaneously, or independently (by release of one or more valves) and the particles in the corresponding regions between arrays flushed out by additional carrier fluid introduced either by the distribution array, or via the sample inlet or buffer inlet(s). New cell samples may then be introduced through the sample inlet and the process may be repeated multiple times to separate large volumes of cells.

General Considerations for Apparatus Fabrication

Multilayer soft lithography (MSL) is a well-known fabrication technique that allows for *facile* and robust fabrication of microfluidic devices having hundreds to thousands of microscopic reaction chambers, valves, pumps, fluidic logic elements and other components. Xia & Whitesides, 1998 (Angewandte Chemie-International Edition 37:551-575; herein incorporated by reference) describe and review procedures, material and techniques for soft lithography, including MSL.

Briefly, the general idea of multilayer soft lithography (MSL) is to iteratively stack layers of polymers, for example PDMS, of varying thickness on top of each other. Thin and thick layers of PDMS with stoichiometric ratios of base and hardener, respectively less and higher than 10:1 are formed on separate wafers. For example, a thinner layer may be obtained using a base:hardener ratio of 20:1 and spun onto a silicon wafer substrate. A thicker layer may be obtained using a base:hardener ratio of 5:1. Photoresist patterns previously made on the wafers will define the microfluidic channels of the device. The thick layer is then peeled away from the wafer and placed on top of the thin wafer. After baking, the excess components in each layer will bond and form a PDMS 'chip' composed of two layers of channels. Methods of working with elastomers and applying them in microfluidic applications are known in the art; see, for example, U.S. Pat. No. 6,929,030; Scherer et al. Science 2000, 290, 1536-1539; Unger et al. Science 2000, 288, 113-116; McDonald et al. Acc. Chem. Res. 2002, 35, 491-499; Thorsen, T. et al, Science 2002, 298, 580-584; Liu, J. et al. Anal. Chem. 2003, 75, 4718-4723; Rolland et al. 2004 JACS 126:2322-2323, PCT publications WO 02/43615 and WO 01/01025.

Various polymers, including but not limited to plastics and soft polymers, may be used in microfluidic devices and systems. Examples of polymers that may be useful in fabrication of all, or a portion of a microfluidic device according to various aspects of the invention include elastomers. Elastomers may be generally characterized by a wide range of thermal stability, high lubricity, water repellence and physiological inertness. Other desirable characteristics of elastomers may vary with the application. It is within the ability of one of skill in the art to select a suitable elastomer or combination of elastomers for the desired purpose. Examples of elastomers include silicone, polydimethylsiloxane (PDMS), photocurable perfluoropolyethers (PFPEs), fluorosilicones, polyisoprene, polybutadiene, polychloroprene, polyisobutylene, polyurethanes, poly(styrene-butadiene-styrene), vinyl-silane crosslinked silicones, and the like. Polymers may be optically clear, or may be opaque, or have varying degrees of transparency. In some embodiments of the invention, it may be desirable to use a biocompatible elastomer. PDMS is one of the first developed and more widely used elastomers in soft lithography applications. Where PDMS is described as the polymer used in various embodiments of the invention, it is for exemplary purposes only, and the choice of alternate polymers is within the knowledge of one skilled in the art. A variety of polymers suitable for use in microfluidic applications, and their various properties and examples of applications are described in U.S. Pat. No. 6,929,030.

Photoresist patterns laid out on a silicon wafer or other suitable support provide a mold for casting the layers. Generally, photoresists may be categorized as positive or negative. Positive photoresist are capable of very fine resolutions. They are highly soluble in alkaline solutions such as KOH; however, photosensitive dissolution inhibitors such as diazonaphthaquinone (DQ) are typically used to block this effect. A photoreaction with ultraviolet (UV) light destroys the DQ and allows the photoresist to be dissolved by the developer solution. The idea of processing this type of photoresist is that all sections exposed to UV light will be removed. An example of a positive photoresist is SPR220-7 (Shipley Company LLC).

Negative photoresist generally comprises a non-photosensitive substrate, a photosensitive cross-linking agent, and a coating solvent. Upon exposure to UV light, the cross-linking agent is activated and causes a hard epoxy to form. The remaining unexposed sections of the photoresist are washed away with the developer solution. SU8 (Micro-Chem) is an example of a negative photoresist that may be used in both MSL molds. In addition, SU8 as an epoxy is very strong and can resist subsequent photolithography processes. Detailed methods and techniques for working with particular photoresists are available from the various manufacturers, and are not addressed further herein. Examples of particular photoresists are for illustrative purposes only, and are not to be considered as limiting of the present invention.

Other components may be incorporated into the microfluidic device during fabrication—hydrodynamic resistance (e.g. serpentine extensions of the channel linking the pump and the separation area to provide additional precision and control of the oscillation pressures), micron-scale valves, pumps, channels, fluidic multiplexers, perfusion chambers and the like may be integrated during MSL. Methods of making and integrating such components are described in, for example, U.S. Pat. Nos. 7,144,616, 7,113,910, 7,040,338, 6,929,030, 6,899,137, 6,408,878, 6,793,753, 6,540,895; US Patent Applications 2004/0224380, 2004/0112442; PCT Applications WO 2006/060748.

Once fabricated, one or more surfaces of a flow channel, via or other space within the microfluidic apparatus may be treated or coated with a surface treatment agent. The surface treatment agent may be a non-biofouling agent. Examples of surface treatment agents may include hydrophilic or hydrophobic compositions, charged, or immunobinding agents, polymers, BSA, or the like that may aid in fluid flow (e.g. reduce fluid friction and/or flow resistance) or prevent the adherence of hydrophobic or hydrophilic components in the carrier fluid or sample, or reduce particle interaction with a surface of the flow chamber, or elements therein such as obstacles, fluid barriers or the like. Examples of polymers include polyethylene glycol of varying polymer MW, such as are available in the art. For example, the channel, via or other space may be temporarily filled with a fluid comprising a surface treatment agent (e.g. to prevent or reduce non-specific adhesion of particles, particularly cells). One of skill in the art will be able to select a suitable polymer size and concentration to deposit sufficient polymer or protein on the surface, while maintaining a suitable viscosity to allow for handling and fluid flow within the device when preparing the treatment. Following treatment of the surface, the flow channel, via or other space may be flushed with a second fluid (e.g. a buffer, media, PBS or the like) to remove any leftover BSA or polymer.

Further aspects and details of particular embodiments of the invention are illustrated, in part, by the following non-limiting methods and examples:

EXAMPLES

Example 1—Fabrication of Silicon Masters

The silicon masters were fabricated in a two-step photo-lithographic process. First, the silicon wafer was coated with a layer of SU-8 negative photoresist (Microchem™) and spun at a speed of 1200 rpm for 50 s. The wafer was then baked on a 95° C. hotplate for 5 minutes and subsequently exposed to UV light through an optical photomask, which was designed using Solidworks™ DWGEditor and commercially-produced by Advance Reproductions (Andover, Mass.). After exposure, the wafer was then baked at 65° C., 95° C., then 65° C. for 1, 4, and 1 minutes respectively. The patterned wafer was developed in SU-8 developer (Microchem) and washed with isopropanol. To harden the patterned microstructures, the wafer was then baked at 200° C. for a period of one hour. The final bake temperature was reached by a slow ramp at a rate of 10 degrees every 12 minutes. After baking, the wafer was allowed to equilibrate to room temperature on top of the hotplate. SPR220-7.0 photoresist (Microchem) was added to the cooled wafer by spin coating at 600 rpm for 50 s. Following spinning, the edge bead was removed from the wafer manually and then softbaked for 1, 5 and 1 minutes at 65° C., 95° C., and 65° C. respectively. A second photomask (CAD/Art Designs) was aligned to the previous set of patterns and subsequently exposed and developed in MF 319 developer (Microchem). Finally, the wafer was baked on a 95° C. hotplate for 5 minutes to allow the SPR220-7.0 photoresist layer to reflow and take on a parabolic profile. Great care is taken throughout the process to prevent exposure of the wafer to thermal shocks which can cause the micro-scale SU-8 features to warp and bend.

The fluid control layer was fabricated on a second silicon master using a single layer of SPR 220-7.0 using the same procedure as described above.

Example 2—Fabrication of PDMS Devices

The PDMS masters were fabricated using standard multi-layer soft lithography techniques as are known in the art for example, as described by Unger et al. 2000 (Science 288: 113) and Studer et al. 2004 (Journal of Applied Physics 95:393). Two layers were formed with a 5:1 base to hardener ratio of RTV 615 silicone (Momentive Performance Materials) for the flow layer and a 20:1 ratio for the control layer. The layers were bonded by diffusion and attached to a glass slide following 45 seconds in an oxygen plasma (Herrick Plasma). Inlets and outlets were punched manually using a 0.5 mm punch (Technical Innovations). A solution of 1% BSA in PBS was used to fill the device prior to operation and incubated for 10 minutes to prevent nonspecific adsorption of cells onto the PDMS surface.

Example 3—Preparation of Cell Samples

Peripheral blood mononuclear cells (PBMCs) were obtained from healthy donors at the Centre for Blood Research (CBR) at The University of British Columbia. L1210 mouse lymphoma cells (MLC) were obtained from culture. MLCs were cultured in suspension using RPMI 1640 (Gibco™, Invitrogen™) with 10% fetal bovine serum and 1% penicillin/streptomycin kept inside an incubator held at 37° C. with 100% humidity and 5% $CO_2$. Prior to experimentation, the cells were concentrated via centrifugation and re-suspended in a solution of phosphate buffered saline (PBS) containing 0.4% bovine serum albumin (BSA) at a concentration of $1 \times 10^7$ cells/ml. Cells were used for experimentation 3-4 days after passaging. In experiments where cells were stained, the L3224 LIVE/DEAD Viability/Cytotoxicity kit (Invitrogen) was used according to the manufacturer's directions. Peripheral blood mononuclear cells were prepared from whole blood obtained from healthy volunteers. Whole blood was drawn into 6 ml sodium heparin containing tubes. PBMCs were separated out using Histopaque 1077 (Sigma-Aldrich) according to the manufacturer's instructions, and then re-suspended at a concentration of $1 \times 10^7$ cells/ml in AIM 5 media (GIBCO-Invitrogen).

Example 4—Deformability Analysis

The pressure differential required to deform single cells was determined using a microfluidic device disclosed herein. The apparatus used in conducting the particle size is illustrated in FIG. 4. The apparatus comprises a central microchannel where funnels with $W_O$=11, 10, 9, 8, 7, 6, 5, 4, 3.5, and 3 μm are arranged in series from the distal end of a microchannel to its center, and then mirrored from the center of the microchannel to the opposing distal end. Using many funnels in one microchannel enables experiments with varying funnel geometries to be conducted on the same cell, while mirroring the funnel chain design at the center of the microchannel eliminates any possible asymmetrical hydrodynamic resistance to the bulk fluid. This design is replicated for funnels tapered at 10°, 5° and 0°. The height of the microchannels is approximately 16 μm, which exceeds the typical diameter of cells used in our experiments.

The chain of funnels is connected to parallel microchannel networks for introducing individual cells from a sample reservoir and for applying an attenuated pressure across the funnel chain. These two networks are isolated from each other using microvalves 425, 426, 427 and 428 so that the introduction of cells and the pressure deformation process can take place independently. Pressure attenuation is accomplished using a fluidic circuit similar to a resistive-divider used in electronic circuits. As shown in FIG. 4, pressure from an external source is applied across points 411 and 412 on a long, possibly serpentine, microchannel. Side branches located at points 413 and 414 are spaced at 1/100 of the distance from 411 to 412, and therefore attenuate the applied pressure by a factor of 100. Microchannel networks connected to the side branch do not significantly affect the pressure drop across 413 and 414 as long as the hydrodynamic resistance of the network is significantly greater than that of the microchannel segment between 413 and 414.

The pressures required to deform single cells through various funnel microstructures were measured using the following process: A single cell was introduced into the main microchannel with valves 425 and 426 sealed, and valves 427 and 428 open. Once the cell flows into the funnel region, the states of all four valves were inverted, exposing the funnel array to the attenuated pressure applied across 413 and 414. This pressure was raised gradually in increments of 5 Pa until the cell successfully transited through successive constrictions. After traversing through a given funnel constriction, the pressure was released and the cell was then given ~30 s to recover its original shape before taking a subsequent measurement. Valves and flow within the device were all pressure-controlled using a combination of custom-built apparatus and a commercial pressure controller (Fluigent™). Experimental data was collected visually on an inverted microscope (Nikon™ Ti-U) with a CCD camera (Nikon DS-2MBW). Static measurements were taken using the image capture software supplied with the camera (Nikon NIS-Elements).

Figure 5A:
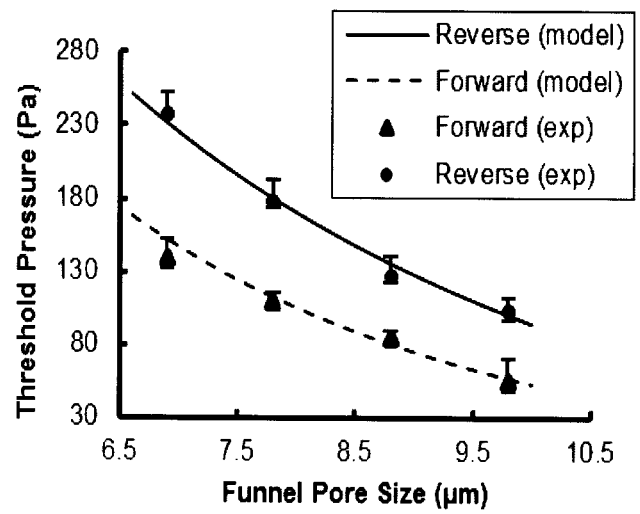
FIG. 5A shows forward and reverse threshold pressures required to deform a single MLC (cell diameter ($\varphi cell$)=15.6 μm) through a 10° funnel constriction. The model curves have been fitted using a cortical tension of 750 pN/μm.
Figure 5B:
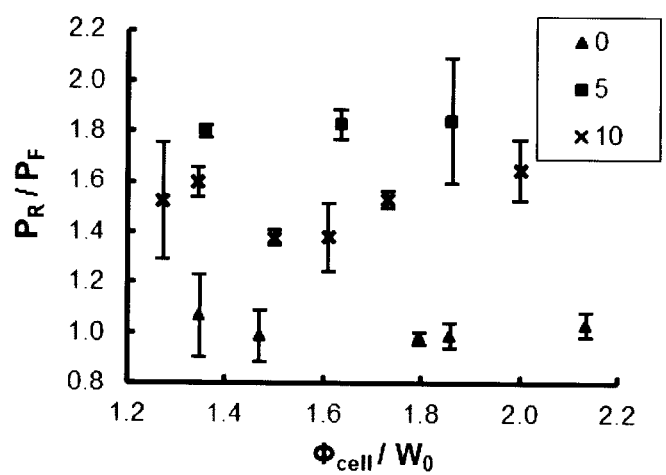
FIG. 5B shows pressure asymmetry for 10°, 5°, and 0° funnel constrictions as a function of $\varphi cell/W_0$. Data points shown are the average pressures from 3-4 measurements on the same cell, while the error bar shows the range of the measured results.

MLCs, with cell diameters ($\varphi_{cell}$) ranging from 8 to 12 μm, were used to study the performance of the funnel ratchet. The forward and reverse threshold pressures required to squeeze single cells through funnel constrictions tapered at 10° plotted as a function of pore size ($W_O$) are shown in FIG. 5(a). The asymmetry between the forward and reverse threshold pressure required for ratcheting is clearly observed. The measured threshold pressures were remarkably repeatable for the same cell, which suggests that this device could be used to study single cell biomechanics in a fashion similar to micropipette aspiration (Hochmuth, R. M., *Micropipette aspiration of living cells*. Journal of Biomechanics, 2000. 33(1): p. 15-22). The liquid-drop model given by equation (1), modified for the constraint provided by the funnel constriction using a similar approach as for tapered micropipettes (Needham, D. and R. M. Hochmuth, *A Sensitive Measure of Surface Stress in the Resting Neutrophil*. Biophysical Journal, 1992. 61(6): p. 1664-1670) has been fitted to the experimental data by adjusting the value of $T_C$. The resulting value for the cortical tension of MLCs is 750 pN/μm, which is comparable with values obtained for mammalian eukaryotic cells in previous studies using micropipette aspiration (Tinevez, J. Y., et al., *Role of cortical tension in bleb growth*. Proc. Natl. Acad. Sci. U.S.A., 2009. 106(44): p. 18581-18586). The pressure asymmetry results measured from the deformation of MLCs are shown in FIG. 5(b) as a non-dimensional plot of the reverse-to-forward pressure ratio ($P_R/P_F$) versus the cell-diameter-to-funnel-opening ratio ($\varphi_{cell}/W_O$) for funnel constrictions tapered at 10°, 5°, and 0°. As expected, smaller funnel angles yield greater asymmetry because of the more gradual taper. The average asymmetry values for the 5° funnel and the 10° funnel are approximately 1.8 and 1.5 respectively. The 0° funnel was a 20 μm long rectangular slot constriction. Deforming cells through these control constrictions showed no pressure asymmetry ($P_R/P_F \approx 1.0$), which confirmed the lack of inherent asymmetries in the measurement apparatus.

These results indicate that a serial array of funnel constrictions may be used in an apparatus for measuring the stiffness of individual particles or cells. When measuring stiffness, it may be absolute, and derived from the pressure required to push the cell through the funnel, or may be relative to a control particle or cell with a defined stiffness.

To study the ratchet transport of single cells in micro-scale funnel constrictions, we designed and fabricated a modified version of the microfluidic device consisting of 37 funnels of identical geometries arranged in series at a pitch of 60 μm. The chain of funnel microstructures was connected to the pressure attenuator and the cell inlet as before. The pressure attenuator contains four additional micro-valves that act as a fluidic H-bridge to enable rapid reversal of the source pressure polarity. Integrating this feature on-chip eliminates the delay associated with inverting the pressure using an external source. Single cells were introduced into this funnel chain through the inlet network. Once a cell reaches the funnel chain, an unbiased oscillatory pressure was applied, while the motion of an individual MLC through the chain of funnel constrictions was tracked by video analysis. The microscope stage was moved manually to follow the motion of the cell while using fiducial markings on the side of the funnel chain to track the position of the cell in the funnel chain.

Figure 6A:
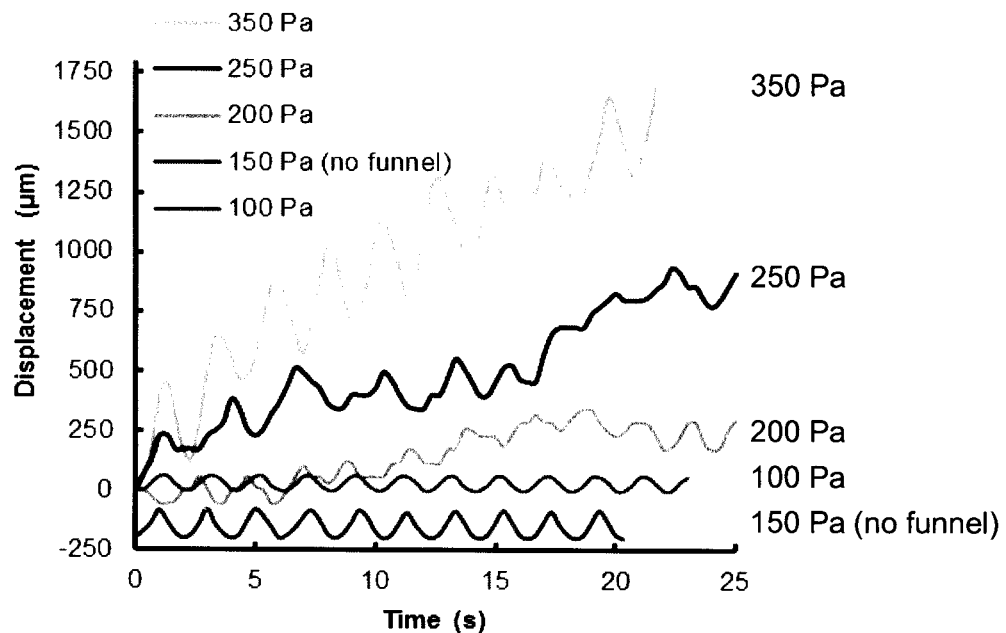
FIG. 6A shows the displacement of a single MLC ($\varphi cell$=10.5 μm) in the funnel chain ($W_0$=6 μm) with a 0.5 Hz oscillation at various pressure amplitudes. An offset has been added to the initial positions of these curves such that they begin at the same point. The 'no funnel' curve is a control experiment that tracks the cell motion in an unconstrained microchannel prior to entering the funnel chain.

The displacements of single MLCs in a funnel chain for several different amplitudes of the square-wave oscillatory pressure are shown in FIG. 6(a). The funnel pore size in this device is 6 μm, while the pressure oscillation frequency is 0.5 Hz. This graph also includes cell displacement data from a control experiment where the oscillatory pressure was applied to a MLC in a section of the central microchannel prior to entering the funnel chain. The unbiased sinusoidal cell displacement shown here confirms the unbiased oscillatory fluid flow of the bulk fluid.

Ratcheting behavior was observed when the pressure amplitude exceeded the threshold required to deform MLCs across a single funnel constriction along the direction of the taper. Specifically, at an amplitude of 100 Pa, cells were confined to oscillate in the region between two funnels, but at 200 Pa and above, the cell began to ratchet forward in the funnel chain in a reliable and deterministic fashion, as shown in FIG. 6(a). The observed threshold for ratcheting was consistent with the forward and reverse pressure thresholds shown in FIG. 5(a), which are 165 Pa and 220 Pa respectively for $\varphi_{cell}$=10.5 μm and $W_0$=6 μm. Above 200 Pa, the cell travels both forward and backwards through several funnel constrictions in each cycle. Ratcheting behavior was preserved at these higher oscillation pressure amplitudes since the asymmetrical threshold pressure enabled these cells to transit through a great number of funnels in the forward direction than the backward direction. The increased applied pressure also increased the net cell velocity. The average flow velocity for pressure amplitudes of 200 Pa, 250 Pa and 350 Pa were 15 μm/s, 30 μm/s, and 60 μm/s respectively.

Figure 6B:
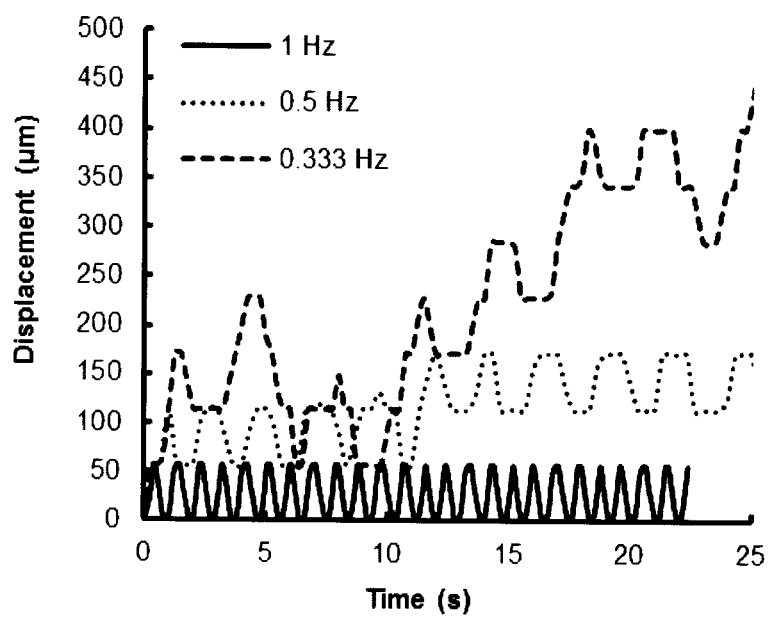
FIG. 6B shows frequency dependence of ratchet motion with an oscillation pressure amplitude of 150 Pa.

The ratcheting behavior was found to depend on oscillation frequency as shown in FIG. 6(b). At a frequency of 1 Hz and an amplitude of 150 Pa, the cells do not have sufficient time to traverse the region between the funnels (~50 μm) and also deform across the funnel. Ratcheting transport was enabled at 0.5 Hz, and proceeded at an increased net forward velocity at 0.333 Hz, suggesting that ~0.5 s was required to complete the process to deform through the funnel constriction. Additionally, the ratcheting process was also dependent on the synchronization between the applied pressure and the location of the cell in a funnel constriction, as well as surface forces between the cell and the microstructure.

Apparatus such as example apparatuses 200, 200A and 700 described above with reference to FIGS. 2, 2A and 7 may also be used for particle deformability analysis. For example, in some embodiments, a population of cells may be infused into a separation chamber and separated according to deformability as described herein, with cells of different deformabilities removed from different outlets. The number of cells removed from each outlet may be used to determine a characteristic deformability distribution in order to evaluate the morphology of the cell population.

Example 5—Particle Separation Analysis

A cell separation apparatus comprising 128 funnels across the width of the separation area in 12 horizontal rows was fabricated. With reference to FIG. 7C, in an example apparatus used in some experiments, the gap g between filter-barrier obstacles is 2 μm, the length l of the passages (and obstacles) in each array is 50 μm, the distance d between arrays is 50 μm, the inlet channel (between filter barrier 750 at the first end and the first array 761) is 100 μm wide (to allow for a greater amount of particles to be sorted per cycle for a given sample concentration), and the separation s (e.g., the horizontal distance from the centre of one passage to the next in each array) is 25 μm. Various experiments were conducted with pressures ranging from 3-50 kPa, and with oscillations of 0.5-2 seconds in the forward direction, and reverse oscillation times ranging from 1-8 seconds. In all cases, the total oscillation time was 1 minute.

To achieve repeatable and consistent sorting, pressure and flow rate applied to the particles within the flow chamber and inside the funnel microstructures needs to be controlled. Too low a pressure will be insufficient to deform the cells through the funnels, while those too high will damage the cells. On-chip valves separate the cell infusion and extraction process from the cell separation process. Valves 738 and 748 placed to the left and right (directional references refer to the example orientation on the drawing sheet containing FIG. 7A) of the separation chamber 702 are used to isolate the loading procedure from the separation procedure. This arrangement provides a purely horizontal flow during loading and purely vertical flow during separation. Valves 713, 715, 723 and 725 above and below the separation chamber are used to quickly switch between forward and backward flow. An oscillating flow is used within the separation area to reduce the occurrence of clogging, biofouling, and inconsistent sorting resulting from cytoskeleton remodeling.

The operation of the device has two stages, a filling stage and a sorting stage. During the filling stage, valves 713, 715, 723 and 725 are closed and equal pressures are applied to both the cell inlet 732 and additional inlets 736 such that the flow is horizontal through the sorting area and cells fill the space (or "row") between the first array 761 and first filter barrier 751. Once this row is filled, valves 738 and 748 are closed, sealing off the sorting area. During the oscillation phase, a constant pressure is applied to both the forward and reverse pressure inlet channels 712 and 722. Valves 713, 715, 723 and 725 act as a fluidic H bridge enabling precise control of the oscillation duration and frequency. For experiments described herein, a forward pressure for 3 seconds followed by a reverse pressure for 1 second was employed, enabling a forward biased motion of the cells through the sorting area. The forward and reverse pressures are equal, and gently deform the cells through the funnel openings as they travel forward through the device. Once the cell distribution within the sorting area has reached steady state, valves 713, 715, 723 and 725 are closed while valves 738 and 748 are opened. This begins the filling stage again, and while the bottom row is filled with new cells, the previously sorted cells are pushed to the right into separate outlets above by the incoming PBS. This process repeats until as many cells as desired have been sorted.

In order to prevent cells from entering the distribution network and being lost from the separation area, filter barriers are placed on either end, or both ends of the separation area within the flow chamber. The blocks employed in the experiments described herein have a semi-circular profile so that any cell which may pass outside of the separation area may more easily squeeze back when the opposite pressure is applied. There is a 2 μm spacing (g in FIG. 7C) between the filter blocks—small enough to prevent the cells used in the experiments described herein from entering.

As the device operates within the laminar regime at low Reynolds number, and flows through rectangular channels, fluid inflow through a single inlet would be a Stokes' flow and achieve a parabolic velocity profile once a steady state is achieved. A 'plug flow' is approximated in the separation chamber via the distribution network and subchannels where the fluid enters the separation chamber—each cell transiting through a pore experiences the same flow rate as every other cell in adjacent pores. The distribution network divides the flow equally among many subchannels, with one subchannel per funnel pore (FIG. 7B), such that the flow exiting these subchannels is comprised of many small parabolic flows of the same magnitude. Thus, the force experienced by a cell at each pore is equal regardless of where that pore is located within the device.

Extended, serpentine microfluidic channels at both ends of the flow channel (FIG. 7A) provide additional hydrodynamic resistance in order to ensure that fluid flow through the apparatus is controlled from a standard pressure source.

PBMCs and MLCs were chosen to validate the operation of the device due to the fact that they have similar but not overlapping size distributions. PBMCs were measured to have a mean diameter of 7.2 μm with a standard deviation of 0.6 μm, whereas the mean diameter of MLCs was measured to be 11.1 μm with a standard deviation of 1.2 μm. These cells also are useful as an indicator of how the device might perform in future applications of separating circulating tumour cells from white blood cells.

When two samples containing equal concentrations of PBMCs and MLCs were combined and the mixture was input into the device the resulting distribution is shown in FIG. 8A. This illustrates a clear separation between the two cell populations within the device, with the peak of the MLC distribution occurring at a funnel opening size of about 9-10 μm and the peak of the PBMC distribution at about 6 μm.

Generally, the sorting area is large enough that only a single cell becomes caught in each funnel, and the smaller cells easily pass through to the smaller funnel rows. In the experiment using both cell types, the MLCs were stained with simple cell stain (Calcein AM, Invitrogen) to clearly differentiate them from the PBMCs. A micrograph of the distribution both in brightfield and under fluorescence is shown in FIGS. 8B and 8C. Only the MLC population is visible under fluorescence, while both populations of cells can be seen in the brightfield. Since each row is essentially may have a separate outlet, the separation boundary can be chosen at any pore size to yield the best separation efficiency. In this particular example, a pore size of 8 μm was used as a 'cut-off' between the two cell populations. FIG. 8D shows a high separation efficiency achieved using the apparatus and cut-off value, with 98% of the MLCs caught in the rows with a pore size of greater than 8 μm ("Trapped at 8-14 μm") and 97% of the PBMCs in the rows with a pore size of less than 8 μm ("Trapped at 2-7 μm").

Figure 9:
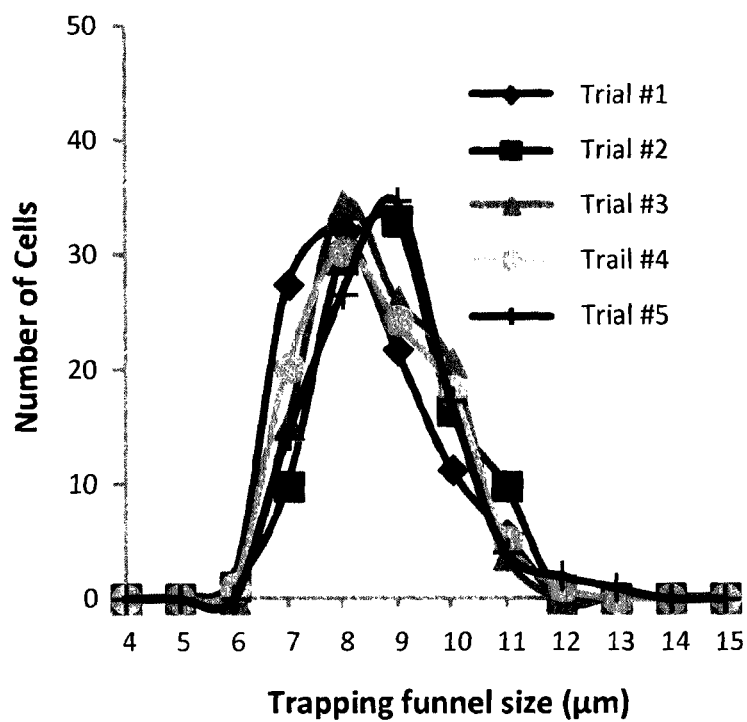
FIG. 9 shows the distribution of mouse lymphoma cells over 5 separate trials. The applied pressure was 14 kPa, with a forward oscillation time of 1 second, and a reverse time of 3 seconds for 1 minute of oscillation.

The repeatability of cell separation is illustrated in FIG. 9. Each trial was conducted in the same device using an applied oscillation pressure of 14 kPa. Some small variations are expected due to the inherent variation in cell sizes from a cultured population. MLCs concentrated in a region of the flow chamber with a pore size of about 8. These results demonstrate a consistent and repeatable cell distribution for a single population.

Figure 10:
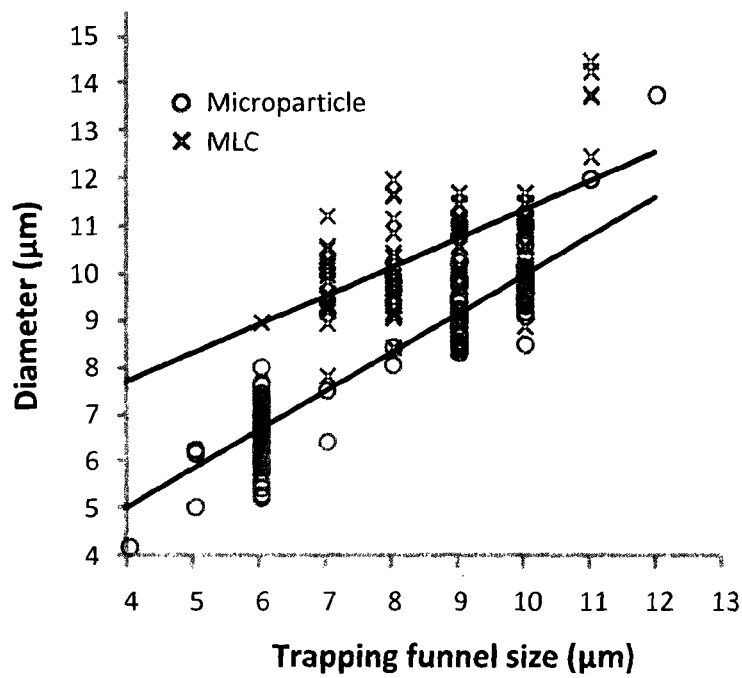
FIG. 10 shows a distribution profile of microparticles and MLCs according to their diameter, relative to funnel size. The applied pressure was 6.9 kPa, with a forward oscillation time of 1 second, and a reverse time of 3 seconds for 1 minute of oscillation.

The resultant distribution of a cell population within the device was found to correspond to the measured size of the cells in suspension. After a sample of MLCs was oscillated for one minute and allowed to reach steady state, the cells were pushed backwards (reverse flow) out of the funnel constriction and given enough time to relax back to their original shape. The radii of the cells were then individually measured using an optical microscope. FIG. 10 shows the results experiments comparing the distribution of MLCs with that of similarly sized polystyrene microparticles sorted under identical conditions. Microparticles (Bangs Laboratories, Fishers, Ind.) with diameters of 6.37±0.48 μm and 10.14±1.04 μm were mixed together to mimic the size range of MLCs. Since polystyrene microparticles are effectively incompressible relative to the polydimethylsiloxane (PDMS) structure, they can be considered to be sorted based on size alone. After sorting (oscillation pressure=14 kPa), the diameters of both MLCs and microparticles were measured (measurement error=±0.8 μm) as a function of their trapping funnel size. The microparticle sizes are strongly correlated to the trapping funnel size with a correlation coefficient of 0.93, where as the corresponding property for MLCs showed a correlation doefficient of 0.65. The reduced correlation is a result of the variability in the deformability of the MLC population. For similarly sized cells and particles, the mean trapping funnel size differed by approximately 2 μm, which suggests that the cells are compressed by this amount on average during the sorting process. These results validate the potential to use our mechanism to sort cells and particles based on size and deformability, therefore expanding the current repertoire of separation methods.

Figures 11A, 11B, 11C, 11D, 11E:
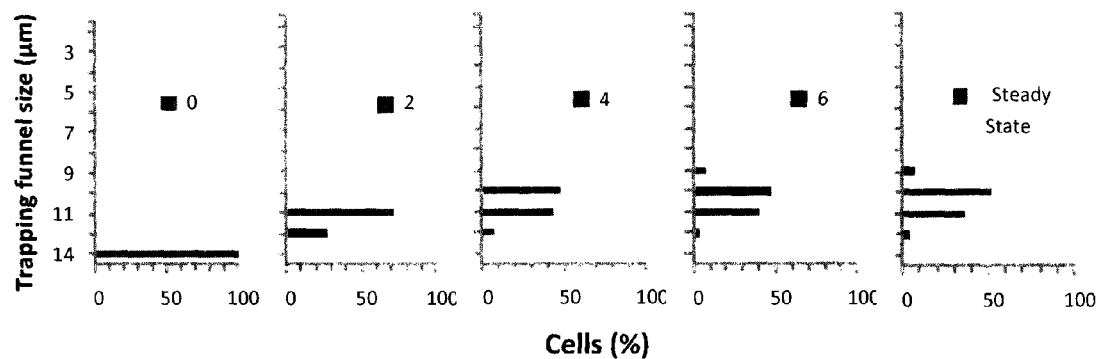
FIGS. 11A-E shows a series of graphs of the distribution of cells in a sample after 0 oscillations (FIG. 11A), 2 oscillations (FIG. 11B), 4 oscillations (FIG. 11C), 6 oscillations (FIG. 11D), and steady state (no further migration of cells, FIG. 11E). The applied pressure was 6.9 kPa, with a forward oscillation time of 1 second, and a reverse time of 3 seconds.

One advantage of the present apparatus is that the steady state distribution is reached quickly. Due to the oscillatory nature of the separation there is little crowding or blocking of funnels, and smaller cells transit easily through the device without being obstructed by large cells. FIG. 11 shows the evolution of a MLC distribution after 0, 2, 4 and 6 oscillations, and a steady state distribution which did not change after 20 oscillations. The entire system reaches steady state after approximately 5 oscillations which corresponds to 20 seconds using an oscillation period of 4 seconds.

Using this example, allowing for 20 seconds to empty the device and bring in a new batch of cells, and using an average of 200 cells sorted in every batch, this gives a theoretical throughput of 500 cells every minute for a single device. The quick sorting time also minimizes the amount of contact between the cells and the funnels which prevents unnecessary stress on the cells and reduces the chance of cellular adsorption to the PDMS surface.

Figure 12:
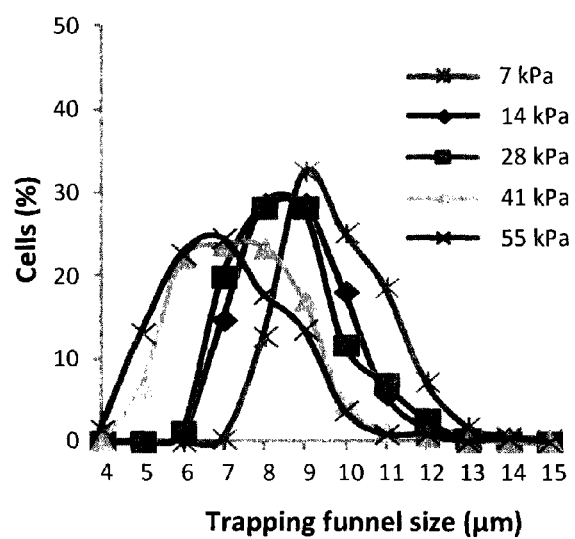
FIG. 12 shows the distribution of cells according to the pressure applied to the flow chamber for 7 kPa, 14 kPa, 28 kPa, 41 kPa and 55 kPa. The oscillation time was 1 second forward and 3 seconds reverse.

We also examined the effects of changing the applied pressure and the period of the oscillation. Increased pressure resulted in a small shift in the distribution of MLCs upwards to smaller funnel sizes as shown in FIG. 12. This suggests that, as greater force is applied to the cells, they can be deformed to a greater extent to pass through smaller openings or funnel sizes. In this way, the applied pressure can be used to 'tune' a specific distribution of cells or particles to concentrate within a range, or above or below a selected funnel size.

Figure 13:
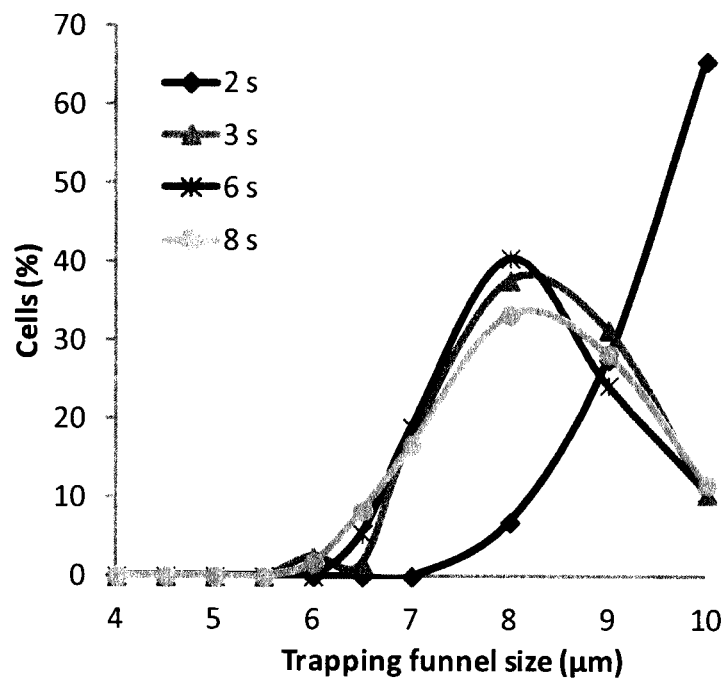
FIG. 13 shows the distribution of cells according to the length of the oscillation cycle for an applied pressure of 10.3 kPa. The forward oscillation time was 1 second, while the reverse time was as noted in the figure for 1 minute of oscillation.

The oscillation period was varied by changing the forward direction time. The backward, or reverse time was left at 1 second to allow the MLCs sufficient time to recover their original shape after being deformed into a funnel, and forward times of 2, 3, 6 and 8 seconds were employed. FIG. 13 shows the distribution of cells according to funnel size for the various forward time oscillations. It can be seen that for forward times longer than 3 seconds, no significant difference was observed in the MLC distribution. However at 2 seconds, the cells did not have sufficient time to deform through the funnel pores and remained caught in larger funnel rows.

To investigate whether this process inflicts any damage upon the cells, a sample of MLCs were stained with a simple live/dead stain (Invitrogen) and oscillated inside the device to ensure that the oscillation process does not damage them. PBS containing additional stain was used as the oscillation media and the cells were incubated for 10 minutes following sorting to allow any cells which had died to absorb the red stain. For oscillation times of 1 minute and applied pressures up to 41 kPa, a cell viability of 99% was observed in all cases. Thus, the normal operating conditions of this device are sufficiently gentle and will not cause any harm to the cells, allowing them to be extracted and re-cultured if desired.

Figure 14:
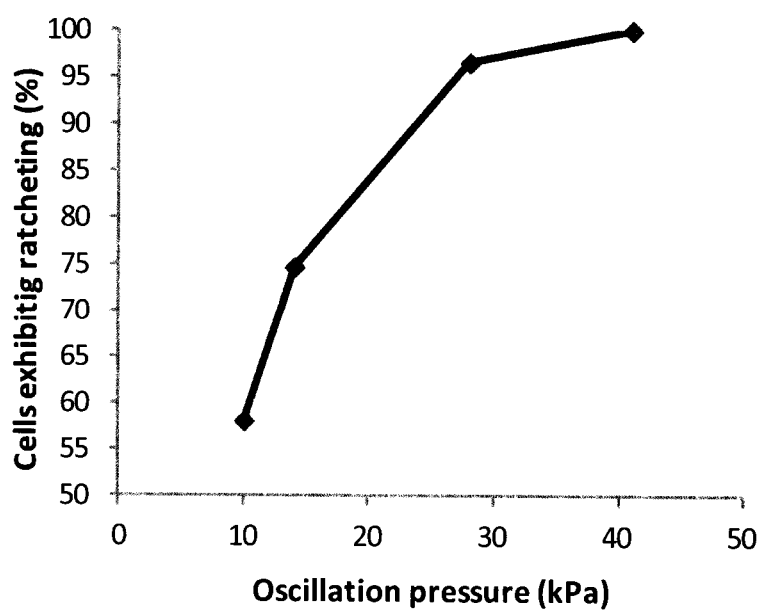
FIG. 14 shows the percentage of cells exhibiting a ratcheting behavior relative to the applied pressure with a forward oscillation time of 1 second, and a reverse time of 3 seconds for 1 minute of oscillation.

The mechanism whereby the cells transit through this device is a ratcheting mechanism. The pores are asymmetrically shaped such that less pressure is required for a cell to transit forward than backward through the opening. To verify this ratcheting behaviour, a sample containing MLCs was brought to steady state after one minute with an oscillation period of 3 seconds forward and 1 second backward. This was then immediately reversed by oscillating at 1 minute with a period of 3 seconds backward and 1 second forward. FIG. 14 shows the percentage of cells that did not return to their original position, but remained caught at various stages in the apparatus, corresponding to the pore size they were unable to traverse. With a pressure of 10.3 kPa applied, over 50% of the cells exhibit ratcheting, and this percentage increases up to 100% with an applied pressure of 41.4 kPa.

High concentrations of cells are desirable to achieve greater throughput, however concentrations that are too high result in device clogging and fouling of the sorting mechanism. This also causes cells to be more likely to adsorb to one another and form aggregates which not only impede their motion through the inlet channel but prevent them from being sorted correctly within the device. Sufficiently high oscillation pressures can often break up these aggregates however this lengthens the sorting process.

Example 6—Red Blood Cell Deformability Analysis

The deformability of red blood cells was evaluated using a microfluidic cell separation apparatus. An apparatus comprising a serial funnel configuration (schematically represented in FIG. 4) was employed, with funnel constructions of $W_0$=0.5, 1, 1.5, 2, 3, 4, 5 and 6, 7 µm in series. As red blood cells are toroid or disc-shaped, rather than generally spherical, in the absence of movement restriction, they may progress through the device as a 'flat' disk (e.g. sideways), or 'on edge' (substantially upright, like a wheel). A channel with a height of about 2-3 µm or less will confine the majority of red blood cells to migrate as a 'flat disk, while a channel with a height greater than about 3-4 µm will allow the red blood cell to migrate in either configuration, or folded or at an angle. Thus, the apparatus was configured to provide a channel depth of about 3 µm, which confines the cell to move flat into the funnel, not to stand up and fold as it traverses through.

The threshold pressure required to push the cell through the funnel is measured as an indicator of the whole cell rigidity or deformability. The minimum applied pressure differential is ~0.3 Pa. Accordingly, the cortical tension of the cell can be measured based on the information of the cell radius, funnel geometry and measured threshold pressure, as governed by equation (1) above derived from Laplace law PMS (phenazine methosulfate) generates superoxide from within the cell in the same way as the auto-oxidation process inside of the sickled red blood cell (RBC). In response to oxidation, the cell membrane stiffens. This induced stiffening may be employed to simulate the microrheologic properties of dense and/or dehydrated sickle cells (Hebbel, R. P., A. Leung, and N. Mohandas, *Oxidation-Induced Changes in Microrheologic Properties of the Red-Blood-Cell Membrane*. Blood, 1990. 76(5): p. 1015-1020, Hebbel, R. P., *The sickle erythrocyte in double jeopardy: autoxidation and iron decompartmentalization*. Seminars in hematology, 1990. 27(1): p. 51-69, and references therein). Here we use microfluidic device to measure the rigidity of PMS treated red blood cells compared to untreated (control) red blood cells, as well as the degree of rigidity change corresponding to different concentration of PMS.

RBCs were suspended at 20% hematocrit in balanced salt solution with antibiotics. The RBC suspensions were then modified with 0, 10, 25, and 50 µM PMS for 60 minutes, followed by dilution 200:1 using phosphate buffered saline for use with the apparatus.

Figure 15:
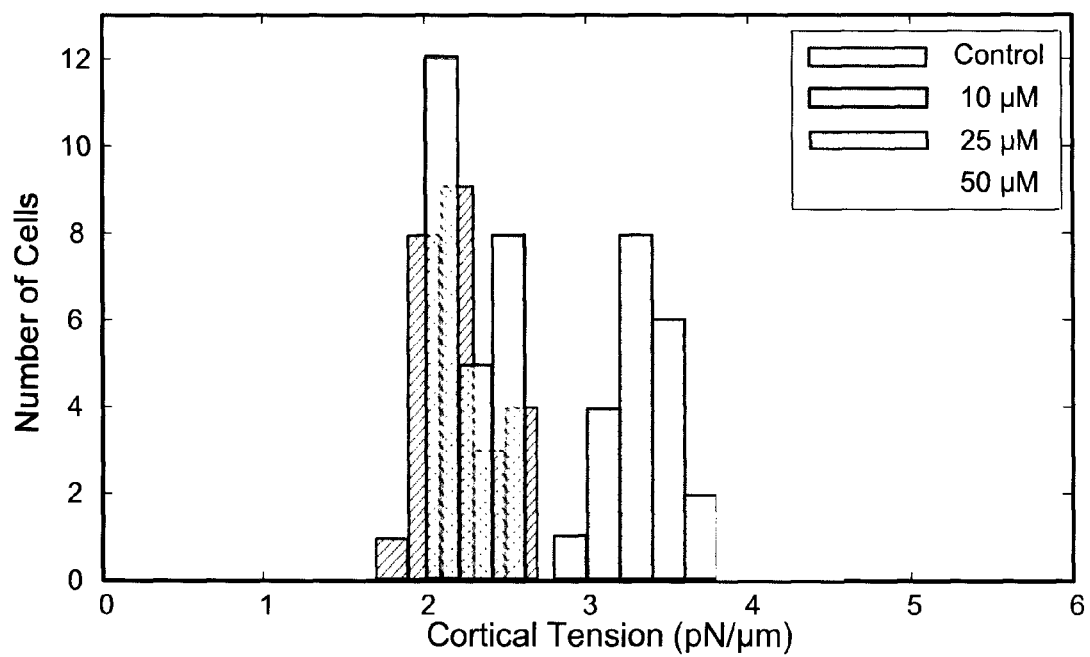
FIG. 15 shows histograms comparing the cortical tensions of red blood cells treated with varying concentrations of PMS (phenazine methosulfate).

The PMS treated RBCs and control RBCs were tested to investigate the effect of PMS on rigidity and/or deformability of the RBCs. Measured threshold pressures are an indication of the changes in deformability. Fresh from the PMS treatment, the red cells exhibits obvious increase in rigidity over normal control RBC. FIG. 15 shows the effects of different concentrations of PMS on red cell rigidity. Threshold pressures were measured of RBC squeezing through 1.1 µm and 1.4 µm constrictions. The value increases as the concentration increases from 0 µM (control), 10 µM, 25 µM to 50 µM. We determined that the deformability of the red cell membrane decreases as the PMS concentration increases and also PMS treated cells exhibit more plastic behaviour than normal healthy red cells. The cortical tension of control RBC and damaged red cells are calculated and shown in Table 1 based on equation (1).

TABLE 1

Average cortical tension calculated based on equation (1), the number behind the value indicates the number of cells tested

|  | Cortical Tension (pN/µm) |
| --- | --- |
| Control RBC | 2.19 ± 0.24 (8) |
| 10 µmol PMS RBC | 2.29 ± 0.19 (7) |
| 25 µmol PMS RBC | 3.38 ± 0.30 (7) |
| 50 µmol PMS RBC | 4.17 ± 0.19 (8) |

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

REFERENCES

1. Astumian, R. D., *Thermodynamics and kinetics of a Brownian motor*. Science, 1997. 276(5314): p. 917-922.
2. Julicher, F., A. Ajdari, and J. Prost, *Modeling molecular motors*. Reviews of Modern Physics, 1997. 69(4): p. 1269-1281.
3. Cranston, H. A., et al., *Plasmodium-Falciparum Maturation Abolishes Physiologic Red-Cell Deformability*. Science, 1984. 223(4634): p. 400-403.
4. Cross, S. E., et al., *AFM-based analysis of human metastatic cancer cells*. Nanotechnology, 2008. 19(38).
5. Nash, G. B., et al., *Abnormalities in the Mechanical-Properties of Red Blood-Cells Caused by Plasmodium-Falciparum*. Blood, 1989. 74(2): p. 855-861.
6. Suresh, S., et al., *Connections between single-cell biomechanics and human disease states: gastrointestinal cancer and malaria*. Acta Biomaterialia, 2005. 1(1): p. 15-30.
7. Lam, W. A., M. J. Rosenbluth, and D. A. Fletcher, *Chemotherapy exposure increases leukemia cell stiffness*. Blood, 2007. 109(8): p. 3505-3508.
8. Bader, J. S., et al., *DNA transport by a micromachined Brownian ratchet device*. PNAS, 1999. 96(23): p. 13165-13169.
9. Gorre-Talini, L., J. P. Spatz, and P. Silberzan, *Dielectrophoretic ratchets*. Chaos, 1998. 8(3): p. 650-656.
10. Rousselet, J., et al., *Directional Motion of Brownian Particles Induced by a Periodic Asymmetric Potential*. Nature, 1994. 370(6489): p. 446-448.
11. Faucheux, L. P., et al., *Optical Thermal Ratchet*. Physical Review Letters, 1995. 74(9): p. 1504-1507.
12. Loutherback, K., et al., *Deterministic Microfluidic Ratchet*. Physical Review Letters, 2009. 102(4): p. 045301.
13. Matthias, S. and F. Muller, *Asymmetric pores in a silicon membrane acting as massively parallel brownian ratchets*. Nature, 2003. 424(6944): p. 53-57.
14. Galajda, P., et al., *Funnel ratchets in biology at low Reynolds number: choanotaxis*. Journal of Modern Optics, 2008. 55(19-20): p. 3413-3422.
15. Hulme, S. E., et al., *Using ratchets and sorters to fractionate motile cells of Escherichia coli by length*. Lab on a Chip, 2008. 8(11): p. 1888-1895.
16. Mahmud, G., et al., *Directing cell motions on micropatterned ratchets*. Nature Physics, 2009. 5(8): p. 606-612.
17. Davis, J. A., et al., *Deterministic hydrodynamics: Taking blood apart*. Proc. Natl. Acad. Sci. U.S.A., 2006. 103(40): p. 14779-14784.
18. Hochmuth, R. M., *Micropipette aspiration of living cells*. Journal of Biomechanics, 2000. 33(1): p. 15-22.
19. Lim, C. T., E. H. Zhou, and S. T. Quek, *Mechanical models for living cells—A review*. Journal of Biomechanics, 2006. 39(2): p. 195-216.
20. Gorre, L., E. Ioannidis, and P. Silberzan, *Rectified motion of a mercury drop in an asymmetric structure*. Europhysics Letters, 1996. 33(4): p. 267-272.
21. Haines, W. B., *Studies in the physical properties of soil V The hysteresis effect in capillary properties, and the modes of moisture distribution associated therewith*. Journal of Agricultural Science, 1930. 20: p. 97-116.
22. Unger, M. A., et al., *Monolithic microfabricated valves and pumps by multilayer soft lithography*. Science, 2000. 288(5463): p. 113-116.
23. Studer, V., et al., *Scaling properties of a low-actuation pressure microfluidic valve*. Journal of Applied Physics, 2004. 95(1): p. 393-398.
24. Groisman, A. and S. R. Quake, *A microfluidic rectifier: Anisotropic flow resistance at low Reynolds numbers*. Physical Review Letters, 2004. 92(9): p. 094501.
25. Needham, D. and R. M. Hochmuth, *A Sensitive Measure of Surface Stress in the Resting Neutrophil*. Biophysical Journal, 1992. 61(6): p. 1664-1670.
26. Tinevez, J. Y., et al., *Role of cortical tension in bleb growth*. Proc. Natl. Acad. Sci. U.S.A., 2009. 106(44): p. 18581-18586.
27. Yap, B. and R. D. Kamm, *Cytoskeletal remodeling and cellular activation during deformation of neutrophils into narrow channels*. Journal of Applied Physiology, 2005. 99(6): p. 2323-2330.
28. Kuo, J. S., et al., *Deformability considerations in filtration of biological cells*. Lab on a Chip, 2010. 10(7): p. 837-842.
29. Hebbel, R. P., A. Leung, and N. Mohandas, *Oxidation-Induced Changes in Microrheologic Properties of the Red-Blood-Cell Membrane*. Blood, 1990. 76(5): p. 1015-1020
30. Hebbel, R. P., *The sickle erythrocyte in double jeopardy: autoxidation and iron decompartmentalization*. Seminars in hematology, 1990. 27(1): p. 51-69.
31. Fehm, T., et al., *Methods for isolating circulating epithelial cells and criteria for their classification as carcinoma cells*. Cytotherapy, 2005. 7(2): p. 171-185. Fehm, T., et al., *Methods for isolating circulating epithelial cells and criteria for their classification as carcinoma cells*. Cytotherapy, 2005. 7(2): p. 171-185.
32. Meng, S., et al., *Circulating tumor cells in patients with breast cancer dormancy*. Clin Cancer Res, 2004. 10(24): p. 8152-62.
33. Guo, Q., S. M. McFaul, and H. S. Ma, *Deterministic microfluidic ratchet based on the deformation of individual cells*. Physical Review E. 83(5).
34. Guo, Q., et al., *Microfluidic Biomechanical Assay for Red Blood Cells Parasitized by Plasmodium falciparum*. Lab on a Chip, 2012. 12(6): p. 1143-1150.
35. McFaul, S. M., B. K. Lin, and H. Ma, *Cell separation based on size and deformability using microfluidic funnel ratchets*. Lab on a Chip, DOI: 10.1039/c2lc21045b, 2012.

All citations are incorporated herein by reference.

What is claimed is:

1. An apparatus comprising:
a flow channel having a first end and a second end;
a fluid flow controller that applies an oscillatory pressure to a carrier fluid in the flow channel to cause the carrier fluid to alternate between flowing in a forward direction from the first end to the second end and flowing in a reverse direction from the second end to the first end;
a microstructure within the flow channel, the microstructure comprising one or more passages therein sized to deform particles in the carrier fluid in the flow channel as the particles pass through the microstructure, wherein each passage is tapered in the forward direction such that less force is required to deform particles passing through the microstructure in the forward direction than to deform particles passing through the microstructure in the reverse direction such that the carrier fluid alternating between flowing in the forward and reverse directions causes net movement of the particles in the forward direction; and
a first filter barrier at the first end of the flow channel.

2. The apparatus of claim 1 wherein the one or more passages comprise funnel shaped passages.

3. The apparatus of claim 2 wherein the funnel shaped passages have a half angle of greater than 0 to about 30 degrees.

4. The apparatus of claim 3 wherein the funnel shaped passages have a half angle of about 10 degrees.

5. The apparatus of any one of claim 1, 2, 3 or 4 wherein the flow channel comprises a separation chamber having opposed sidewalls extending from the first end to the second end, and wherein the microstructure comprises an array of obstacles extending between the sidewalls of the separation chamber, the array of obstacles arranged to provide passages between adjacent pairs of obstacles, wherein the obstacles are shaped such that the passages are tapered in the forward direction.

6. The apparatus of claim 5 comprising:
- a sample inlet for introducing particles into the separation chamber between the first end and the array;
- a first sample outlet for removing particles from the separation chamber between the first end and the array; and
- a second sample outlet for removing particles from the separation chamber between the array and the second end.

7. The apparatus of claim 1 wherein the microstructure comprises a plurality of arrays of obstacles extending between the sidewalls of the separation chamber.

8. The apparatus of claim 7 wherein each array of obstacles is configured to provide a corresponding set of passages between adjacent pairs of obstacles, wherein the obstacles are shaped such that the passages are tapered in the forward direction, and such that the passages decrease in size in each successive array from the first end to the second end.

9. The apparatus of claim 7 wherein the plurality of arrays comprise arrays with different spacing between obstacles.

10. The apparatus of claim 9 wherein the spacing between obstacles in each of the plurality of arrays is largest in the array closest to the first end and smallest in the array closest to the second enc.

11. The apparatus of claim 1 comprising a second filter barrier at the second end of the flow channel.

12. The apparatus of claim 11 wherein the first filter barrier comprises a plurality of filter barrier obstacles having gaps therebetween.

13. The apparatus of claim 12 wherein the gaps between the filter barrier obstacles are aligned with the passages of the microstructure.

14. The apparatus of claim 1 comprising a first distribution network for introducing carrier fluid at the first end, the first distribution network comprising a plurality of subchannels aligned with the passages of the microstructure.

15. The apparatus of claim 14 comprising a second distribution network for introducing carrier fluid at the second end, the second distribution network comprising a plurality of subchannels aligned with the passages of the microstructure.

16. The apparatus of claim 1 wherein the one or more passages are configured to exclude passage of one or more of: leukocytes, embryonic cells, stem cells, progenitor cells, metastatic cells, cancerous cells and dead cells.

* * * * *